(12) United States Patent
Kilian et al.

(10) Patent No.: US 7,056,936 B2
(45) Date of Patent: *Jun. 6, 2006

(54) SYNERGISTIC COMBINATION

(75) Inventors: Ulrich Kilian, Reichenau (DE); Christian Schudt, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/437,005

(22) Filed: May 14, 2003

(65) Prior Publication Data

US 2004/0034087 A1    Feb. 19, 2004

Related U.S. Application Data

(63) Continuation of application No. 10/049,999, filed as application No. PCT/EP00/07852 on Aug. 11, 2000, now Pat. No. 6,624,181, which is a continuation-in-part of application No. 09/367,850, filed as application No. PCT/EP98/01047 on Feb. 24, 1998, now Pat. No. 6,333,354.

(30) Foreign Application Priority Data

Aug. 21, 1999  (EP)  ................................. 99116447

(51) Int. Cl.
*A61K 31/137*  (2006.01)
*A61K 31/44*   (2006.01)

(52) U.S. Cl. ...................... 514/352; 514/653
(58) Field of Classification Search ................ 514/653, 514/352, 263.34, 300, 339, 351, 568
See application file for complete search history.

(56) References Cited

U.S. PATENT DOCUMENTS

| | | | |
|---|---|---|---|
| 3,840,537 A | 10/1974 | Garside et al. | 544/184 |
| 3,941,785 A | 3/1976 | Clarke et al. | 514/826 |
| 4,400,506 A | 8/1983 | Lal et al. | 544/246 |
| 4,992,474 A * | 2/1991 | Skidmore et al. | 514/653 |
| 5,602,110 A | 2/1997 | Drumm et al. | 514/47 |
| 5,712,298 A * | 1/1998 | Amschler | 514/352 |
| 5,795,564 A | 8/1998 | Aberg et al. | 424/45 |
| 5,804,588 A | 9/1998 | Dyke et al. | 514/314 |
| 6,288,118 B1 | 9/2001 | Nieman et al. | 514/572 |

FOREIGN PATENT DOCUMENTS

| | | |
|---|---|---|
| FR | 2390164 | 12/1998 |
| WO | 00/67741 A2 | 11/2000 |

OTHER PUBLICATIONS

Torphy, T.J., et al. "Stimulation of *Beta* Adrenoceptors in a Human Monocyte Cell Line (U937) Up-Regulates Cyclic AMP-Specific Phosphodiesterase Activity", *Journal of Pharmacology and Experimental Therapeutics*, vol. 263, pp. 1195-1205, (1992).

Maesen, B.L.P., et al., "Effects of formoterol in apparently poorly reversible chronic obstructive pulmonary disease", *Eur Respir J*, vol. 13, pp. 1103-1108, (1999).

Campillo, N., et al., "Novel bronchodilators in the treatment of asthma and COPD", *Expert Opin. Ther. Patents*, vol. 12, No. 1, pp. 53-63, (2001).

Tanizawa, M., et al., "Phosphodiesterase IV Inhibitors Synergistically Potentiate Relaxation Induced by Forskolin in Guinea-Pig Trachea", *Clinical and Experimental Pharmacology and Physiology*, vol. 25, pp. 114-119, (1998).

Au, B-T, et al., "Effect of PDE4 inhibitors on zymosan-induced IL-8 release from human neutrophils: synergism with prostanoids and salbutamol" *British Journal of Pharmacology*, vol. 123, pp. 1260-1266, (1998).

Giembycz, M.A., "Phosphodiesterase 4 and tolerance to $\beta_2$-adrenoceptor agonists in asthma", *TiPS*, vol. 17, pp. 331-336, (1996).

Krasnowska, M., et al., "Treatment of Bronchial Asthma with Low Doses of Papaverine Combined with BETA Stimulators", *PNEUM. POL.*, No. 1-2, pp. 21-24, (1982).

Turner, N.C., et al., "Relaxation of guinea-pig trachea by cyclic AMP phosphodiesterase inhibitors and their enhancement by sodium nitroprusside", *Br. J. Pharmacol.*, vol. 111, pp. 1047-1052, (1994).

Rasmussen, J.B., et al., "Additive Bronchodilator Effects of Terbutaline and Enprofylline in Asthma", *Eur J Clin Pharmacol*, vol. 32, pp. 23-26, (1987).

Persson, C.G.A., et al., "Tracheal Relaxation from Combinations of Xanthines and of a $\beta_2$-Receptor Agonist and Xanthines", *Lung*, vol. 164, pp. 33-40, (1986).

* cited by examiner

Primary Examiner—Phyllis G. Spivack
(74) Attorney, Agent, or Firm—Nath & Associates PLLC; Joshua B. Goldberg; Sheldon M. McGee

(57) ABSTRACT

The invention relates to the combined administration of PDE inhibitors and $\beta_2$ adrenoceptor agonists for the treatment of respiratory tract disorders.

9 Claims, No Drawings

SYNERGISTIC COMBINATION

This application is a continuation of U.S. patent application Ser. No. 10/049,999 filed Feb. 20, 2002 now U.S. Pat. No. 6,624,181 under 35 U.S.C. § 371 from International Application No. PCT/EP00/07852, bearing an International Filing date of Aug. 11, 2000 and a Priority Date of Aug. 21, 1999, which is a Continuation-in-Part of U.S. patent application Ser. No. 09/367,850, now U.S. Pat. No. 6,333,354, filed on Aug. 27, 1999 under 35 U.S.C. § 371 from International Application No. PCT/EP98/01047, bearing an International Filing Date of Feb. 24, 1998, the contents of which is hereby incorporated by reference in its entirety.

FIELD OF APPLICATION OF THE INVENTION

The invention relates to the combination of certain known active compounds for therapeutic purposes.

The substances used in the combination according to the invention are known active compounds from the PDE inhibitors class and active compounds from the $\beta_2$ adrenoceptor agonists class. Their combined use in the sense according to the invention for therapeutic purposes has not yet been described in the prior art.

DESCRIPTION OF THE INVENTION

It is the object of the present invention to make available respiratory tract therapeutics which fulfill the following conditions:
  Good antiinflammatory action
  Marked bronchorelaxation and —dilatation
  Good oral availability, at least with respect to the PDE inhibitor
  Minor side effects
  Good suitability for long-term therapy
  Favorable influence on bronchial hyperreactivity.

It has now been found that the combined use of a PDE inhibitor which can be used as a respiratory tract therapeutic and of a $\beta_2$ adrenoceptor agonist outstandingly fulfills the abovementioned conditions.

The invention thus relates to the combined use of a PDE inhibitor which can be used as a respiratory tract therapeutic and a $\beta_2$ adrenoceptor agonist in the treatment of respiratory tract disorders.

PDE inhibitors which can be used as respiratory tract therapeutics in the sense of the present invention are those compounds which slow the breakdown of cyclic AMP (cAMP) or cyclic GMP (cGMP) by inhibition of the phosphodiesterases, which can lead to a relative increase in the intracellular concentration of cAMP or cGMP.

Possible PDE inhibitors within the meaning of the present invention are primarily those substances which are to be considered part of the PDE4 inhibitor class and those substances which can be designated as mixed types of PDE3/4 inhibitors. By way of example, those PDE inhibitors may be mentioned which are described or claimed in the following patent applications and patents: DE 1545687, DE 2028869, DE 2123328, DE 2315801, DE 2402908, DE 2413935, DE 3900233, EP 0103497, EP 0139464, EP 0158380, EP 0163965, EP 0335386, EP 0389282, EP 0428302, EP 0435811, EP 0459505, EP 0470805, EP 0490823, EP 0506194, EP 0511865, EP 0527117, EP 0557016, EP 0626939, EP 0664289, EP 0671389, EP 0685474, EP 0685475, EP 0685479, EP 0736532, EP 0738715, EP 0748805, EP 0763534, EP 0816357, EP 0819688, EP 0819689, EP 0832886, EP 0834508, EP 0848000, JP 92234389, JP 94329652, JP 95010875, JP 98072415, JP 98147585, U.S. Pat. No. 5,703,098, U.S. Pat. No. 5,739,144, WO 9117991, WO 9200968, WO 9212961, WO 9307146, WO 9315044, WO 9315045, WO 9318024, WO 9319068, WO 9319720, WO 9319747, WO 9319749, WO 9319751, WO 9325517, WO 9402465, WO 9412461, WO 9420455, WO 9422852, WO 9427947, WO 9501338, WO 9501980, WO 9503794, WO 9504045, WO 9504046, WO 9505386, WO 9508534, WO 9509623, WO 9509624, WO 9509627, WO 9509836, WO 9514667, WO 9514680, WO 9514681, WO 9517392, WO 9517399, WO 9519362, WO 9520578, WO 9522520, WO 9524381, WO 9527692, WO 9535281, WO 9535283, WO 9535284, WO 9600218, WO 9601825, WO 9606843, WO 9611690, WO 9611917, WO 9612720, WO 9631486, WO 9631487, WO 9635683, WO 9636595, WO 9636596, WO 9636611, WO 9636625, WO 9636638, WO 9638150, WO 9639408, WO 9640636, WO 9703967, WO 9704779, WO 9705105, WO 9708143, WO 9709345, WO 9712895, WO 9718208, WO 9719078, WO 9720833, WO 9722585, WO 9722586, WO 9723457, WO 9723460, WO 9723461, WO 9724117, WO 9724355, WO 9725312, WO 9728131, WO 9730999, WO 9731000, WO 9732853, WO 9735854, WO 9736905, WO 9743288, WO 9744036, WO 9744322, WO 9747604, WO 9748697, WO 9804534, WO 9805327, WO 9806692, WO 9806704, WO 9807715, WO 9808828, WO 9808830, WO 9808841, WO 9808844, WO 9809946, WO 9809961, WO 9811113, WO 9814448, WO 9818796, WO 9821208, WO 9822453, WO 9845268, WO 9855481, WO 9856756, WO 9905111, WO 9905112, WO 9505113, WO 9906404 and WO 9918095. Those PDE inhibitors are to be emphasized which are claimed in the patent applications or patents EP 0393500, EP 0510562, EP 0553174, WO 9501338, WO 9603399, WO 9636625, WO 9636626, WO 9735854, WO 9821208, WO 9831674, WO 9840382, WO 9855481, WO 9905111, WO 9905112, WO 9905113, WO 9931071 and WO 9931090. Substances having good oral availability are preferred here.

Exemplary PDE inhibitors are shown on the following pages with the aid of their formulae:

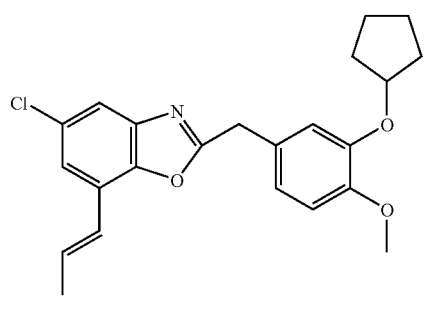

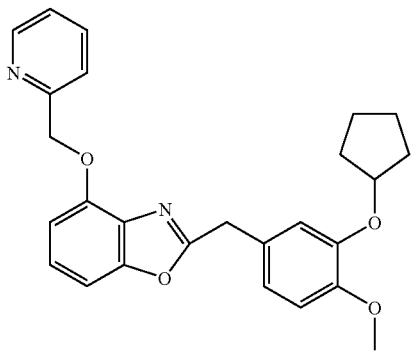

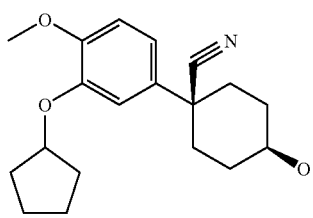
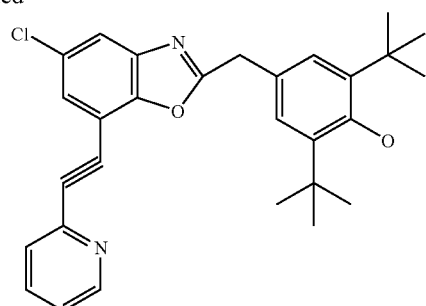
-continued
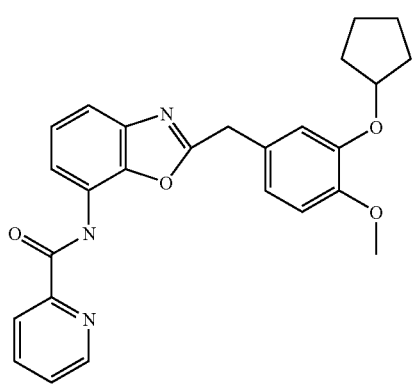
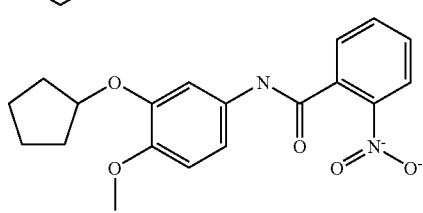
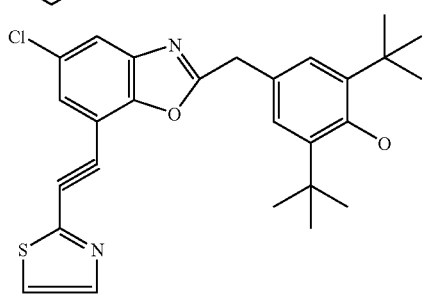
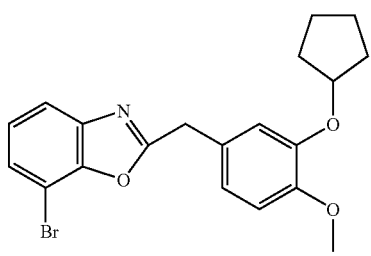
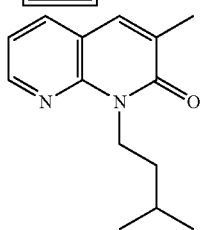
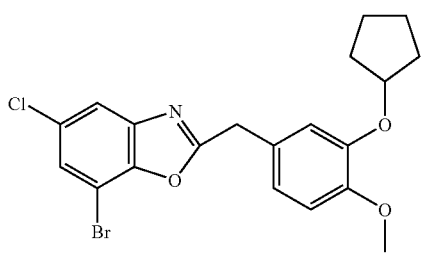
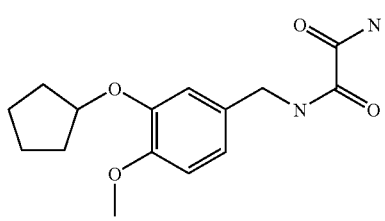
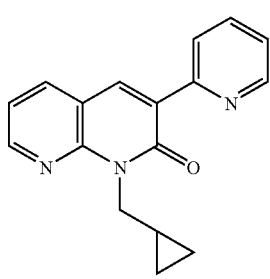
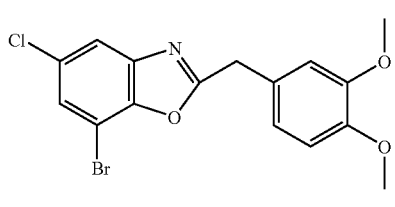
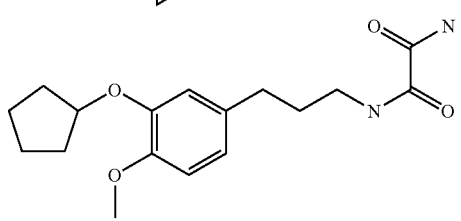

-continued
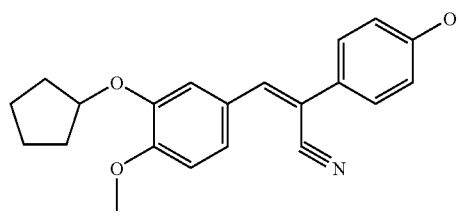
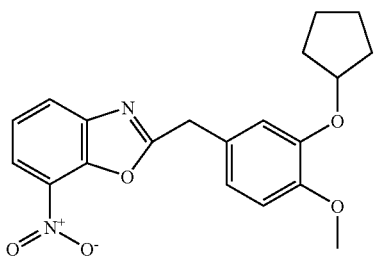
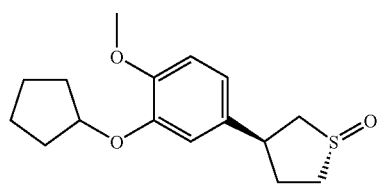
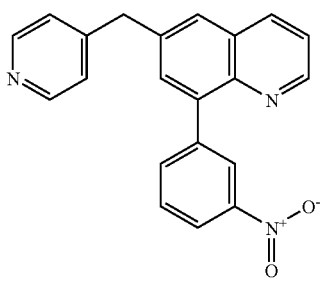
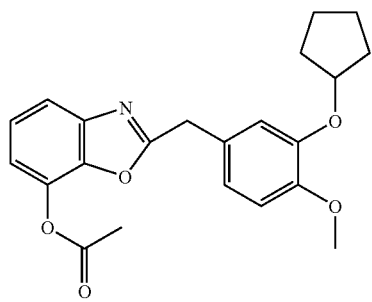
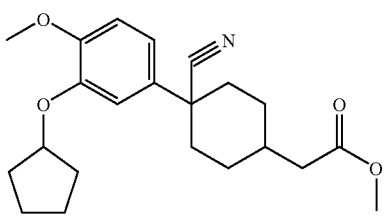
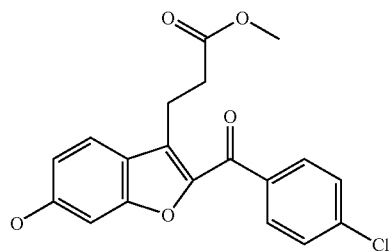
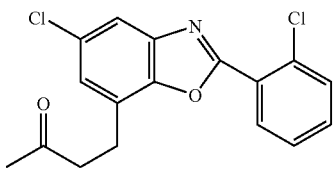
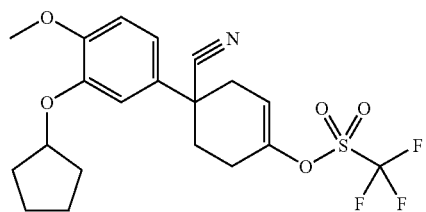
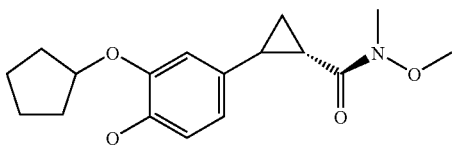
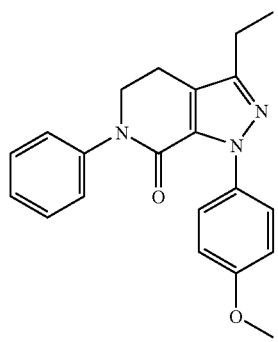
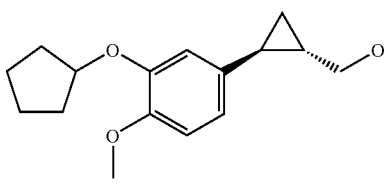

-continued
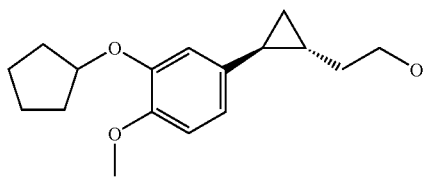
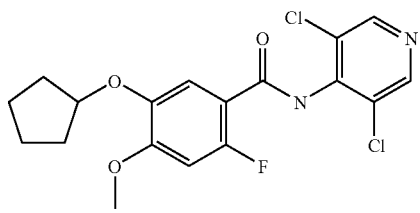
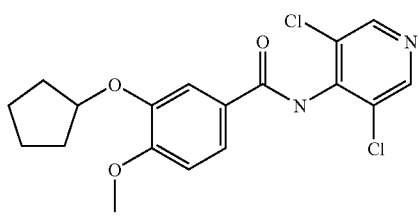
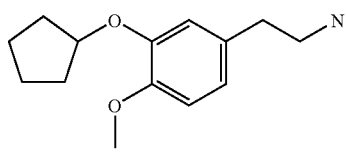
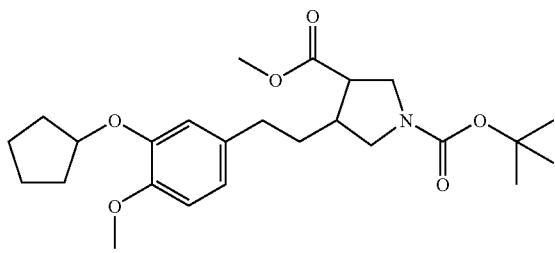
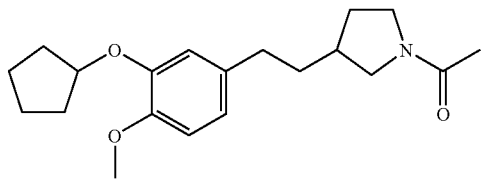
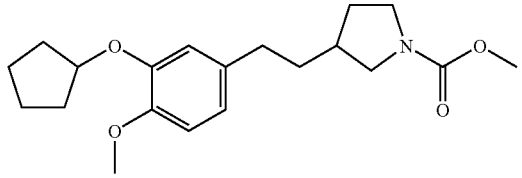
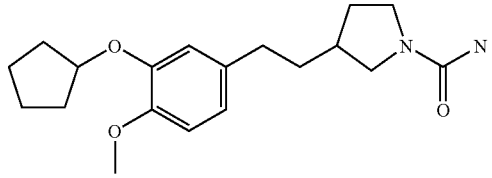
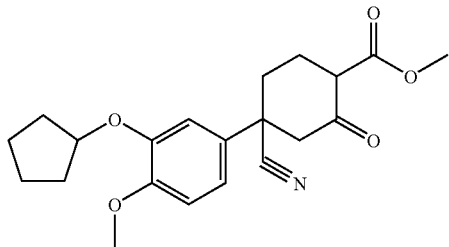
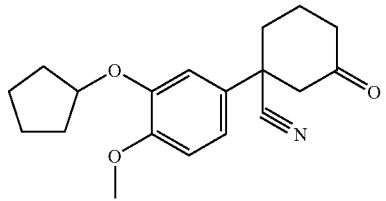
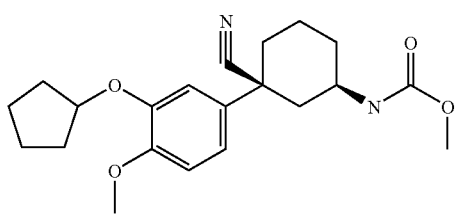
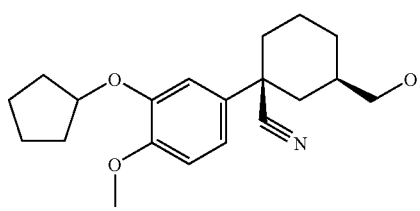
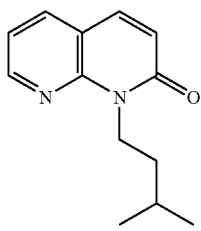
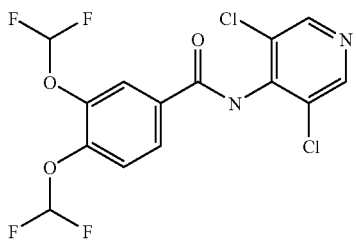

-continued
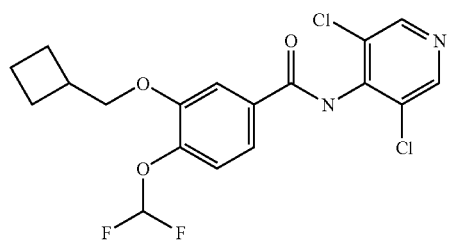
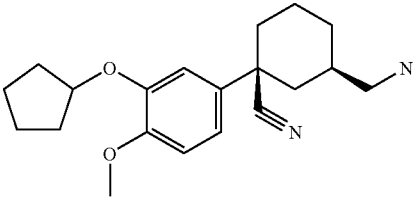
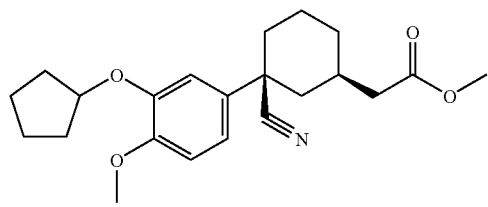
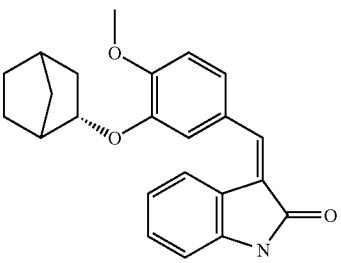
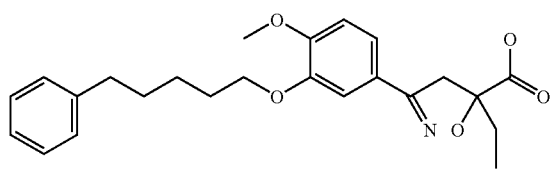
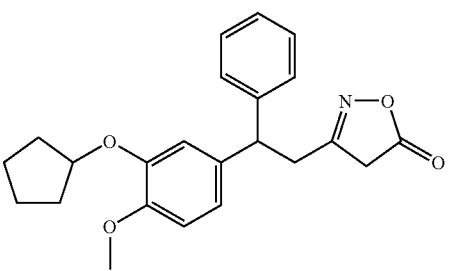
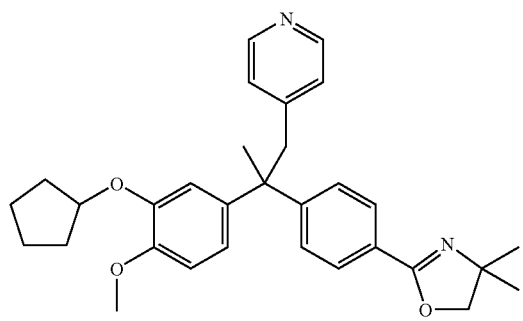
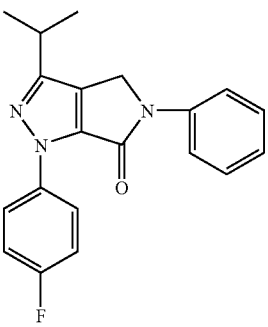
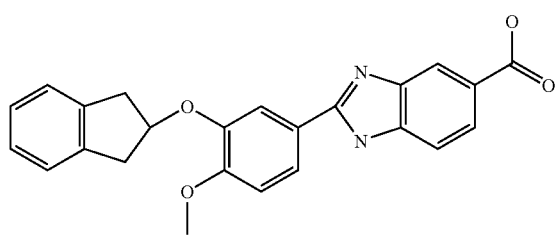
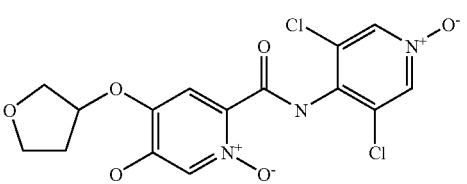
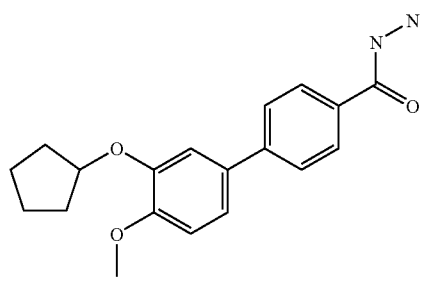
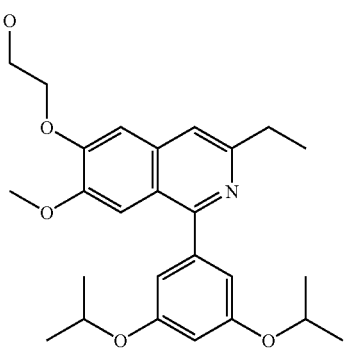

11 12
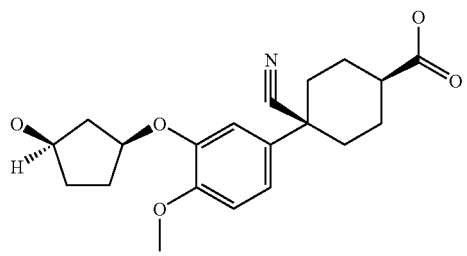
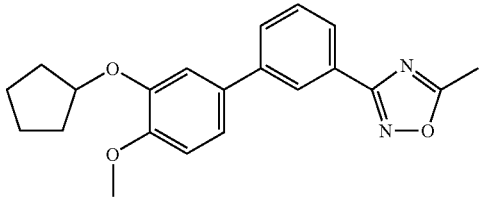
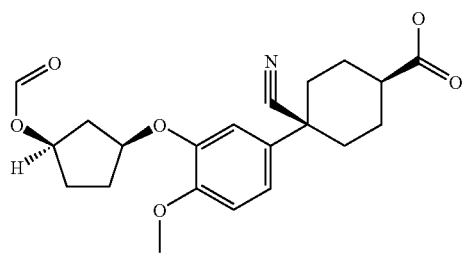
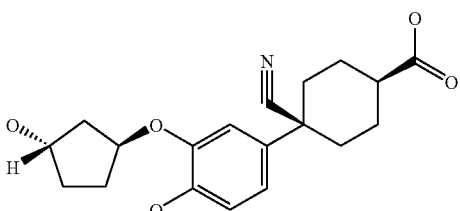
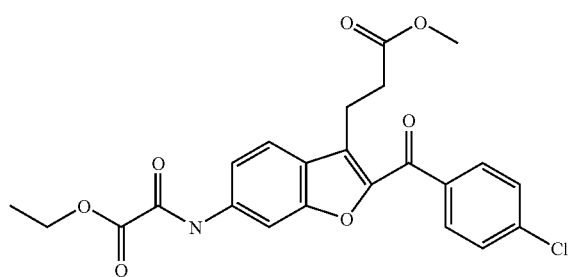
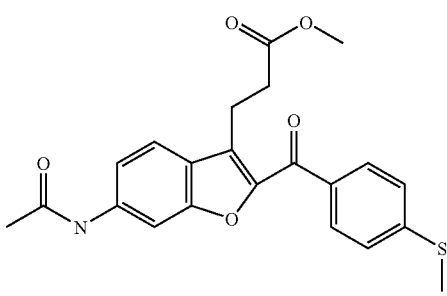
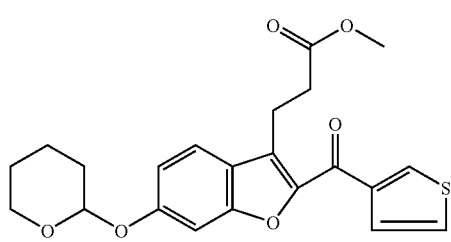
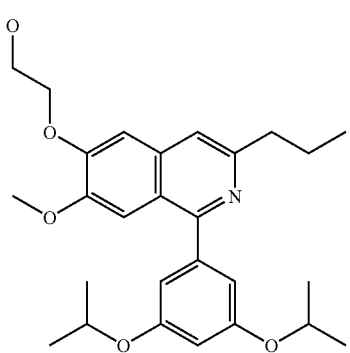
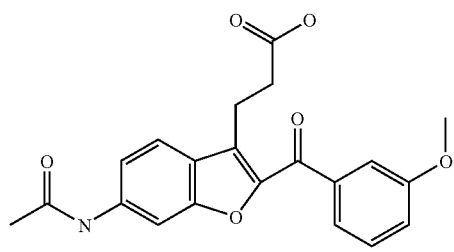
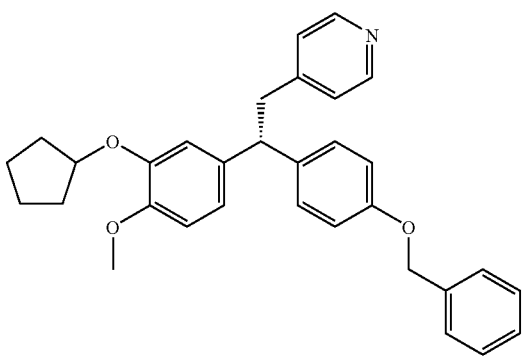
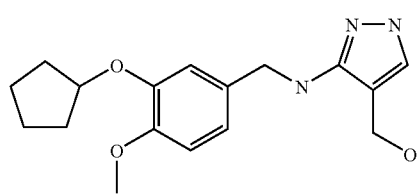
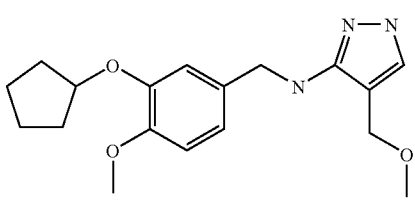

-continued
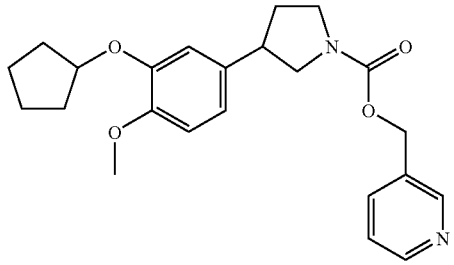
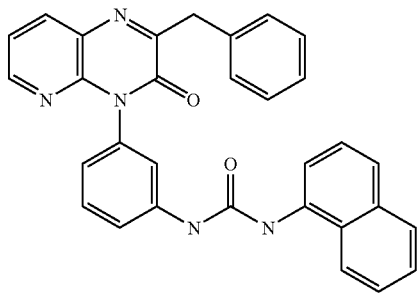
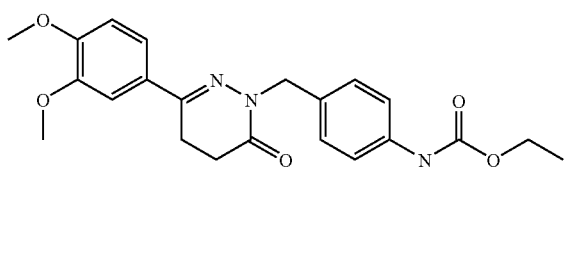
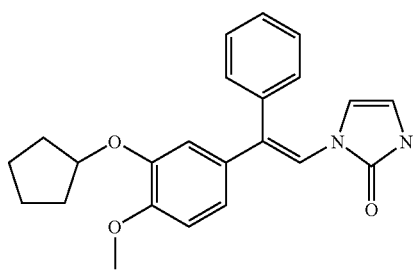
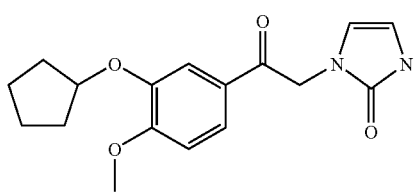
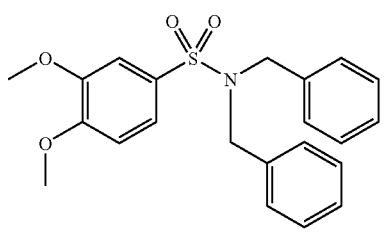
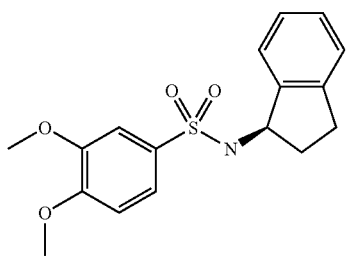
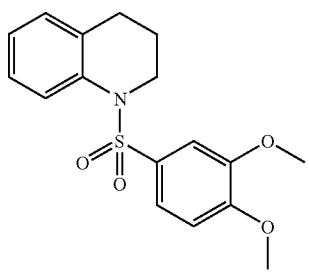
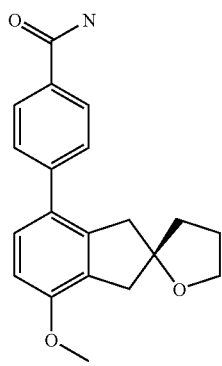
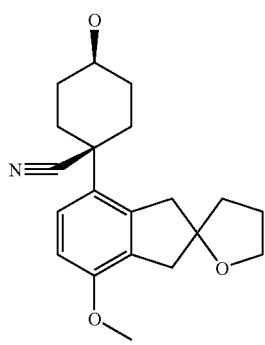

-continued
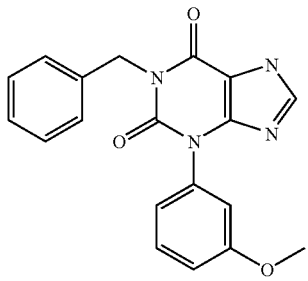
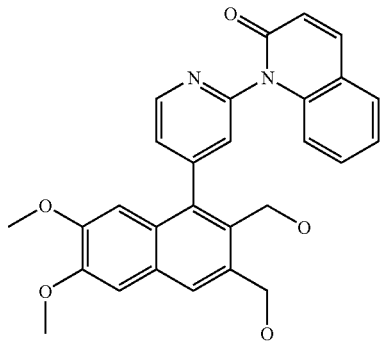
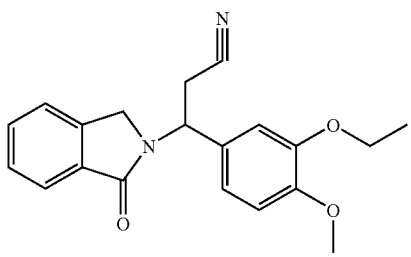
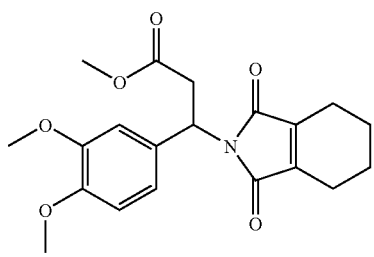
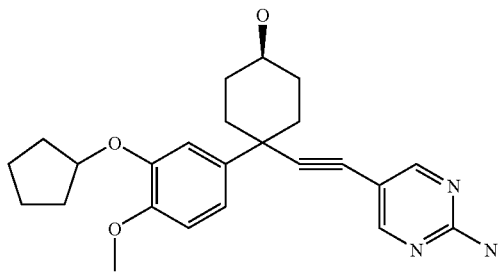
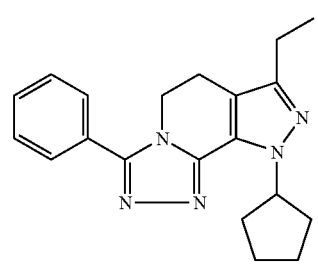
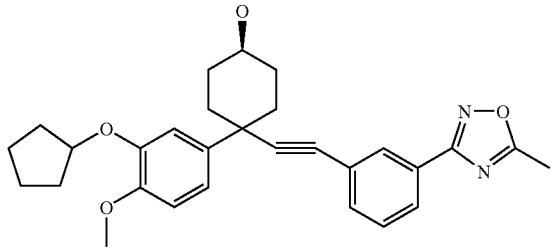
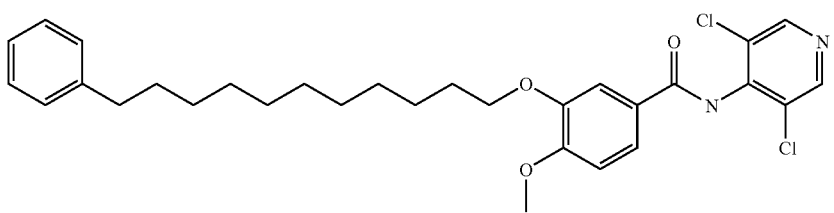
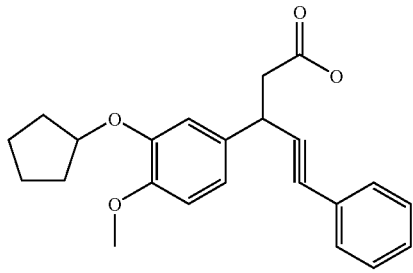
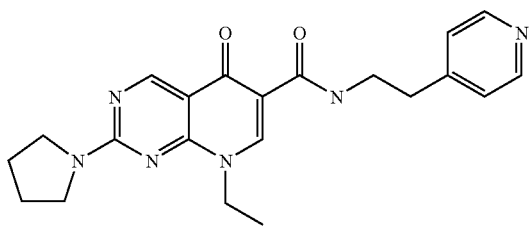

-continued
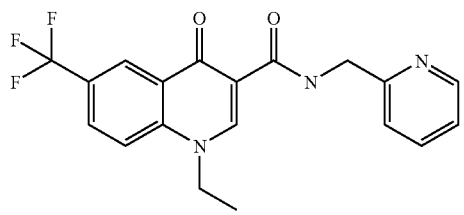
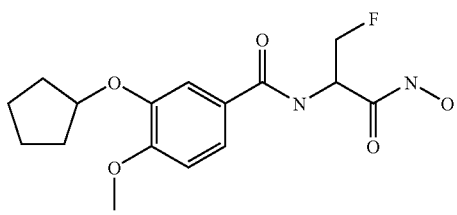
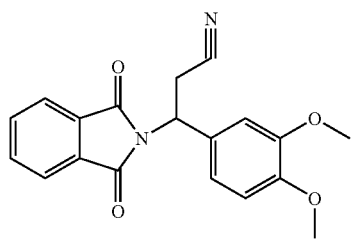
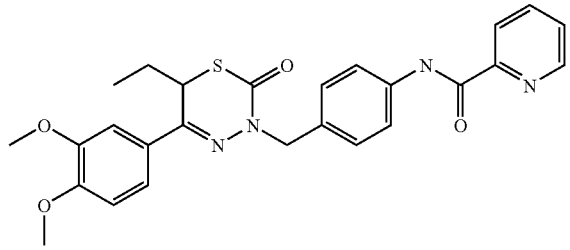
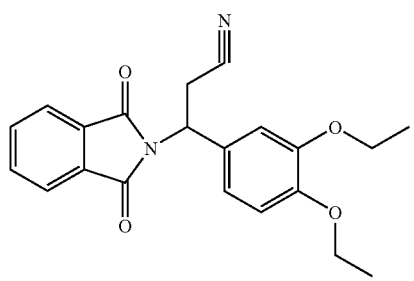
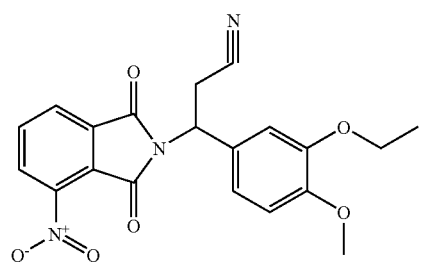
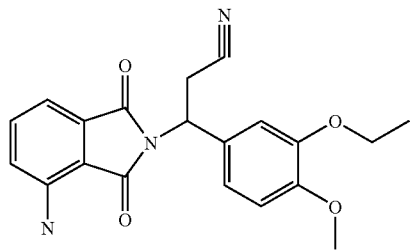
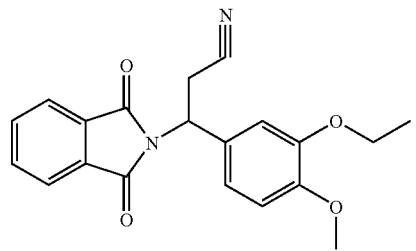
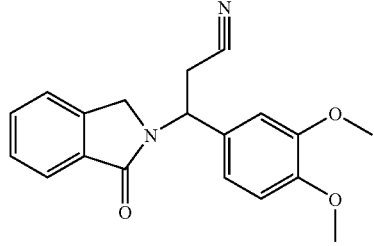
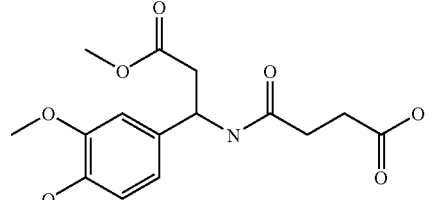
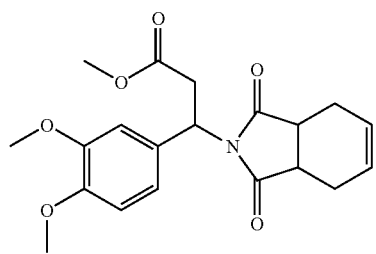
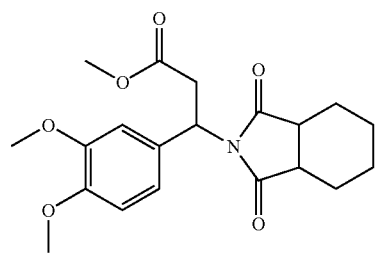

-continued
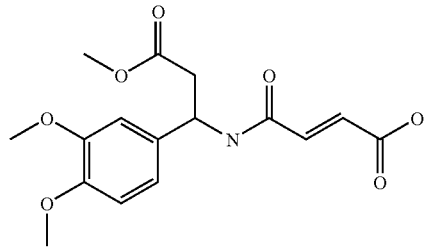
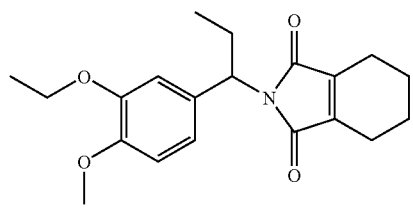
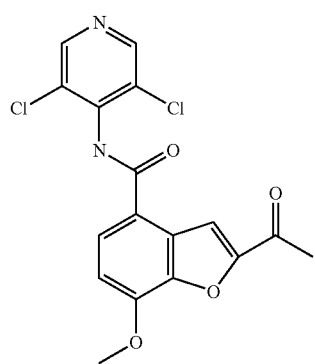
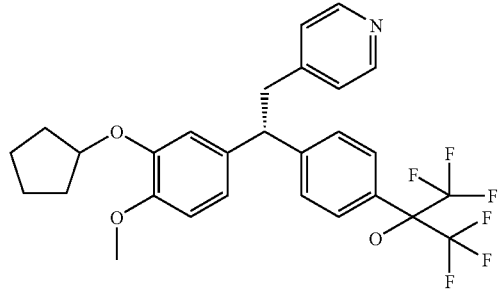
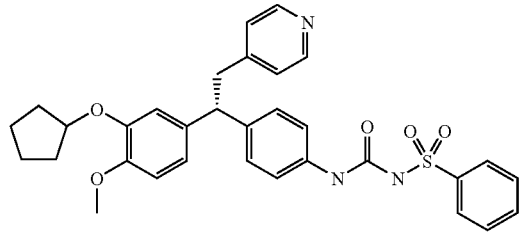
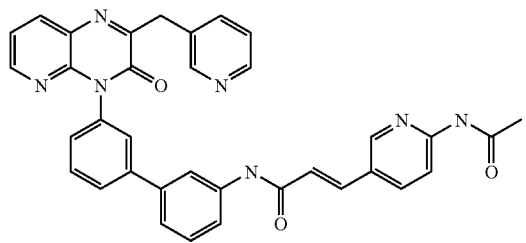
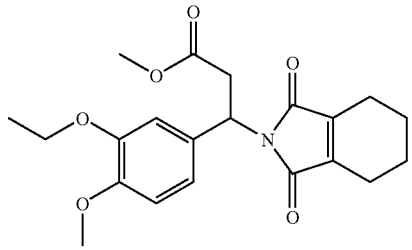
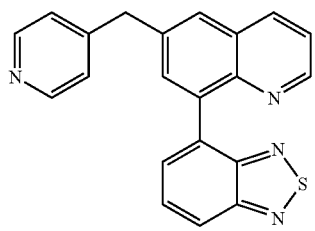
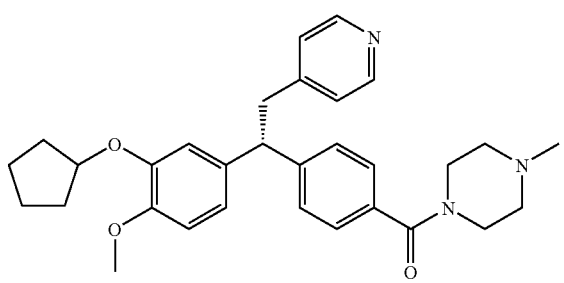
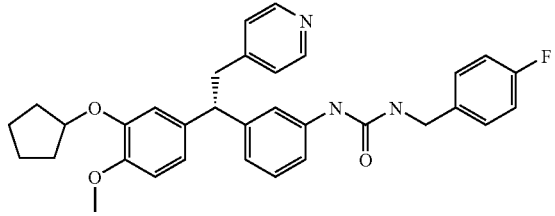
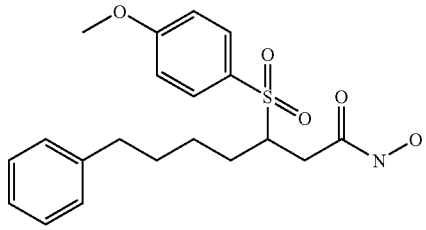
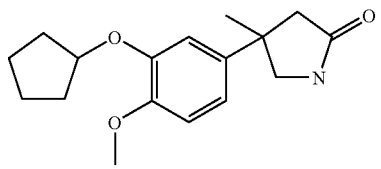

-continued
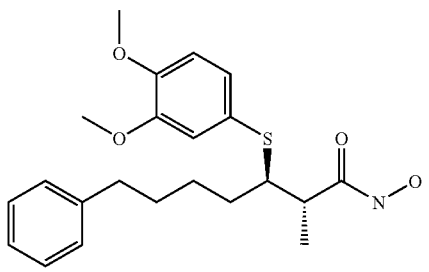
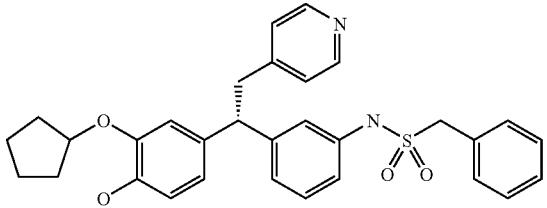
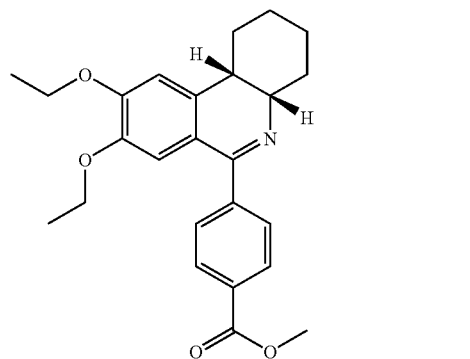
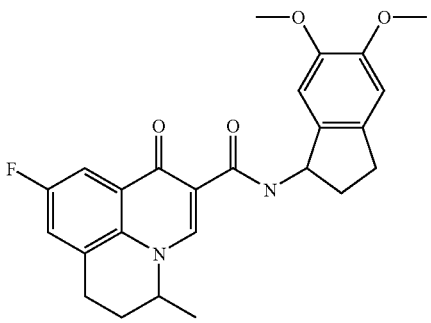
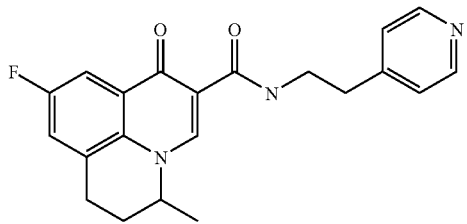
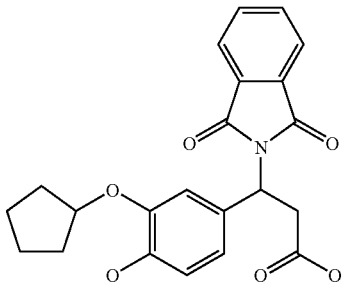
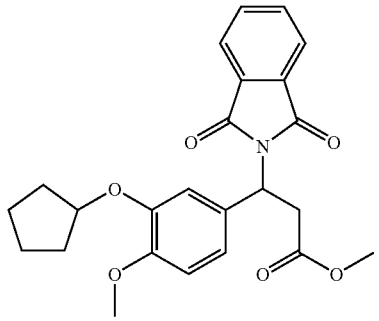
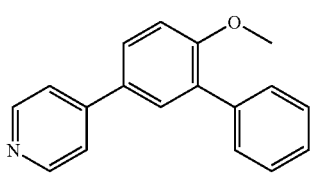
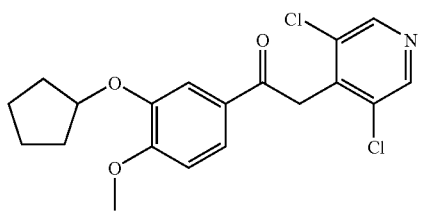
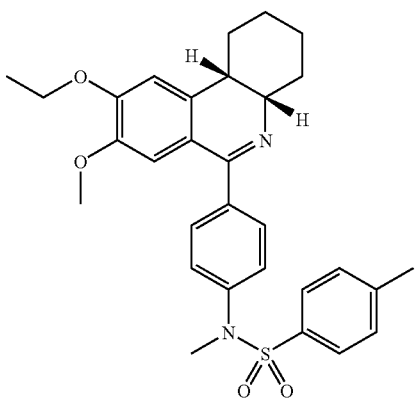

-continued
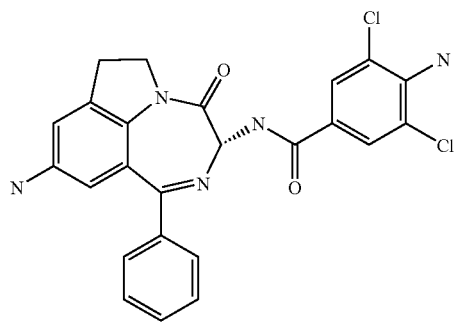
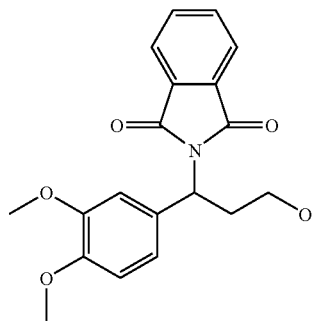
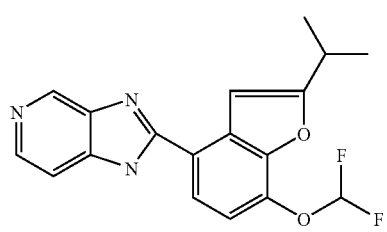
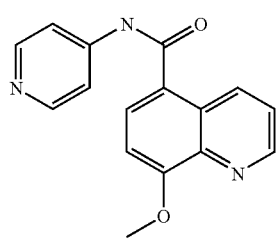
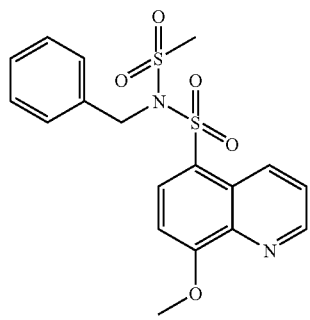
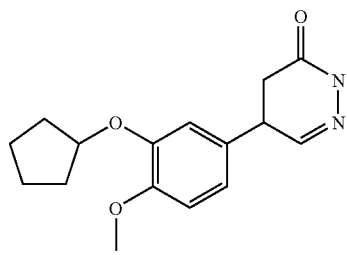
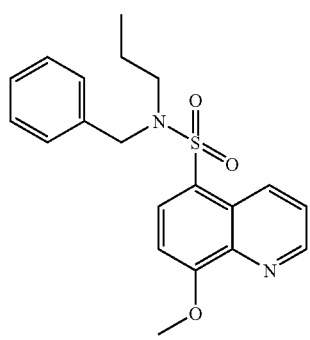
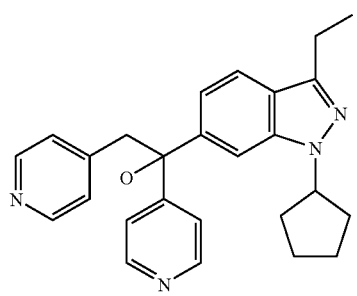
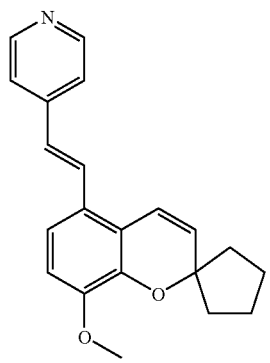
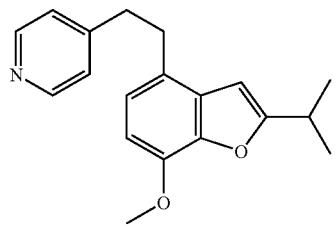

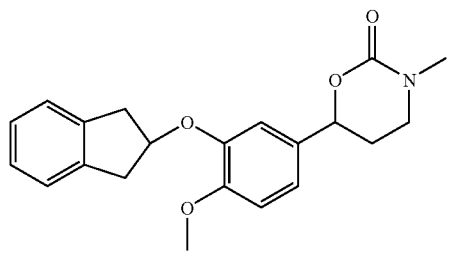
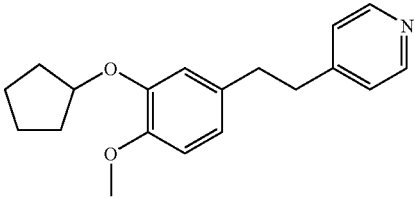
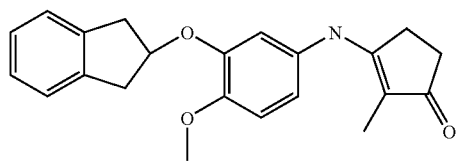
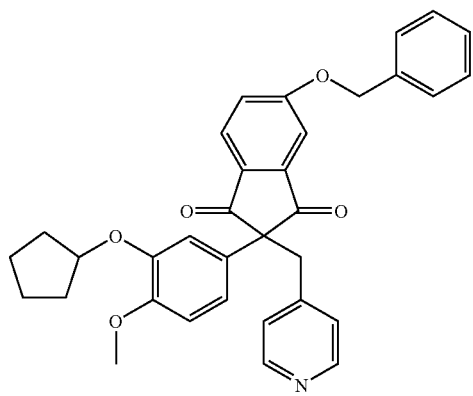
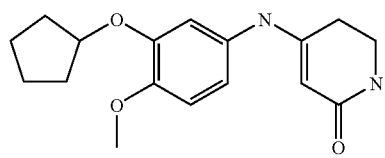
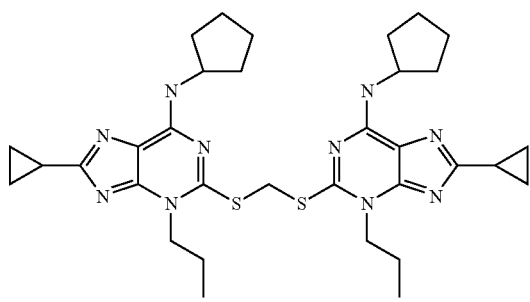
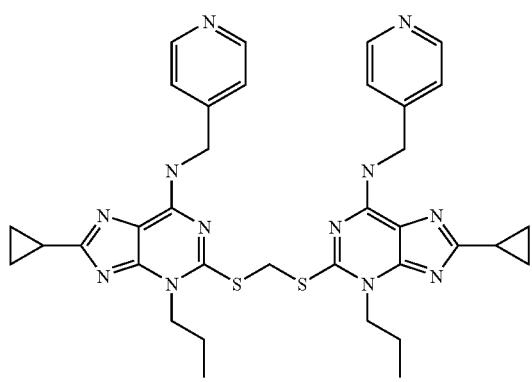
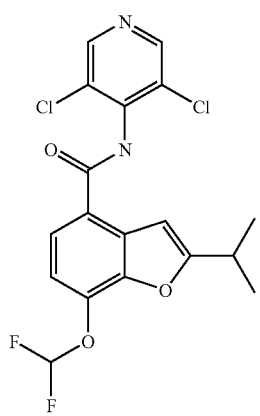
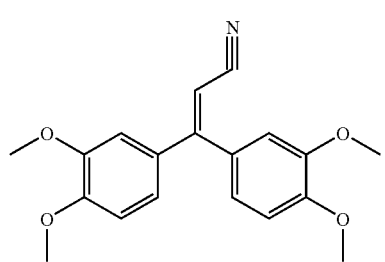
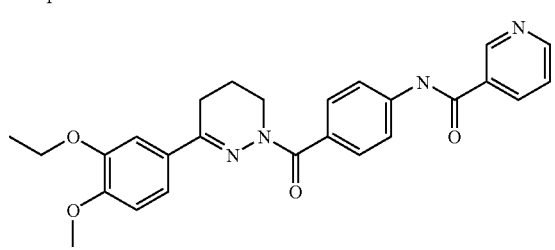

-continued
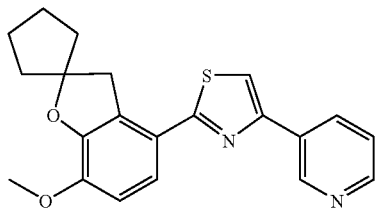
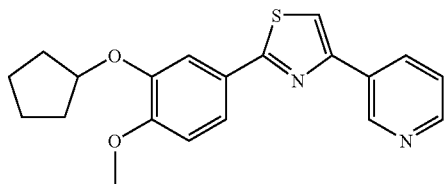
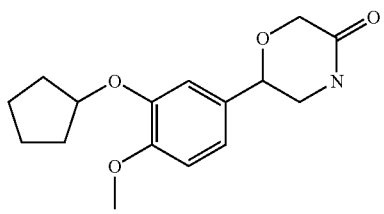
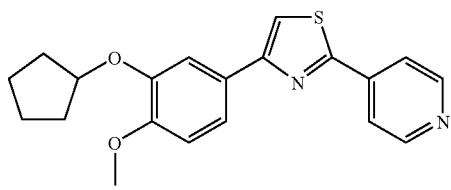
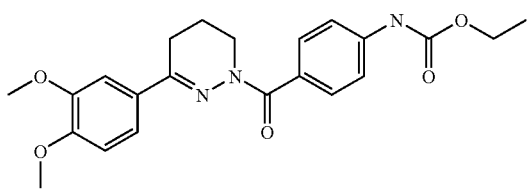
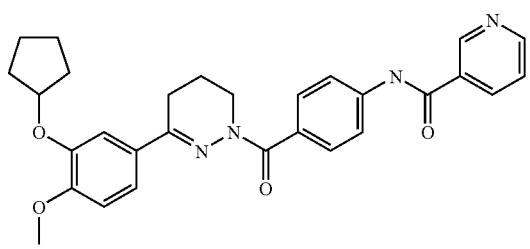
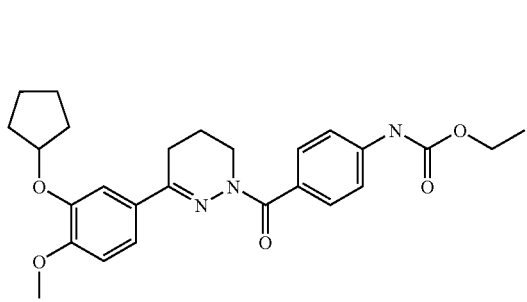
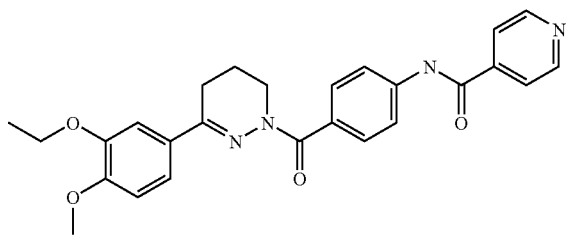
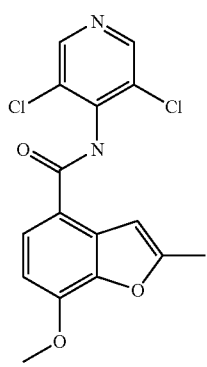
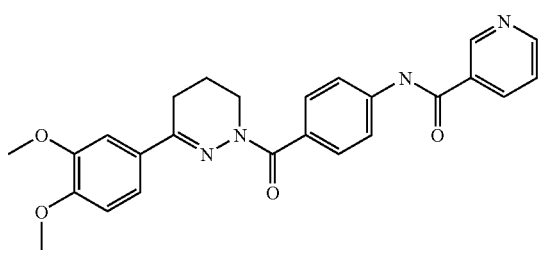
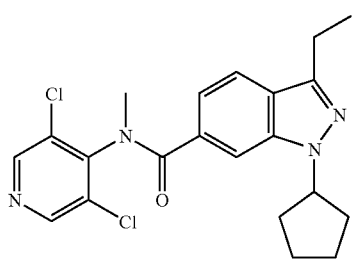
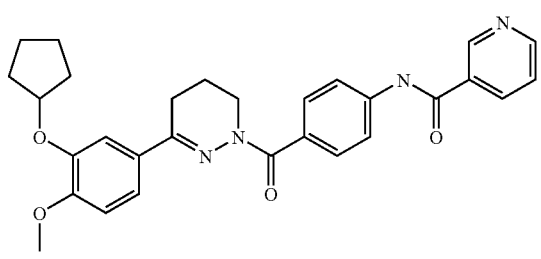

-continued
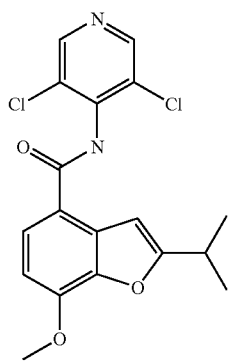
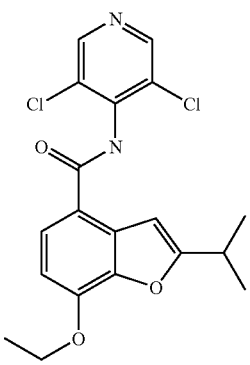
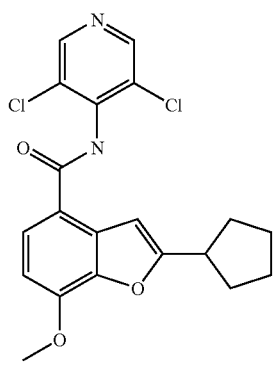
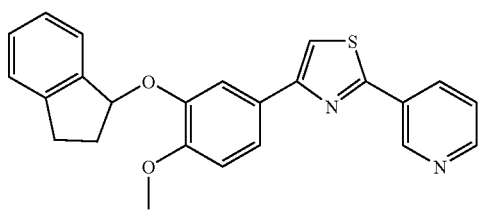
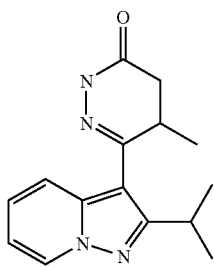
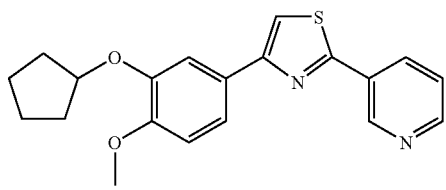
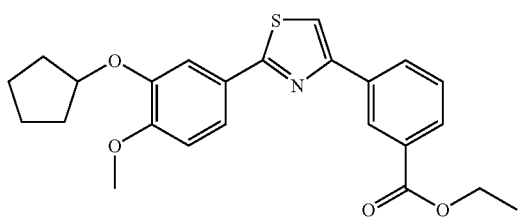
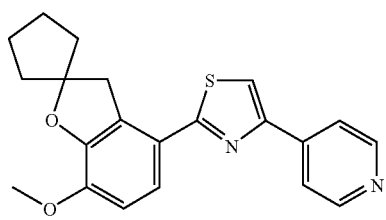
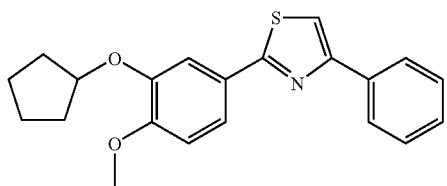
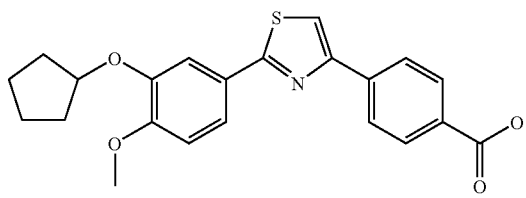
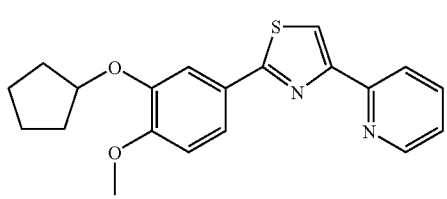
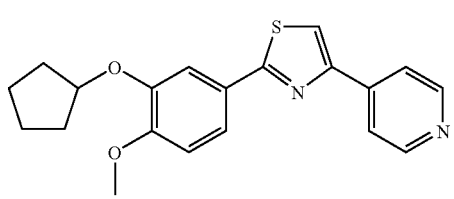

-continued
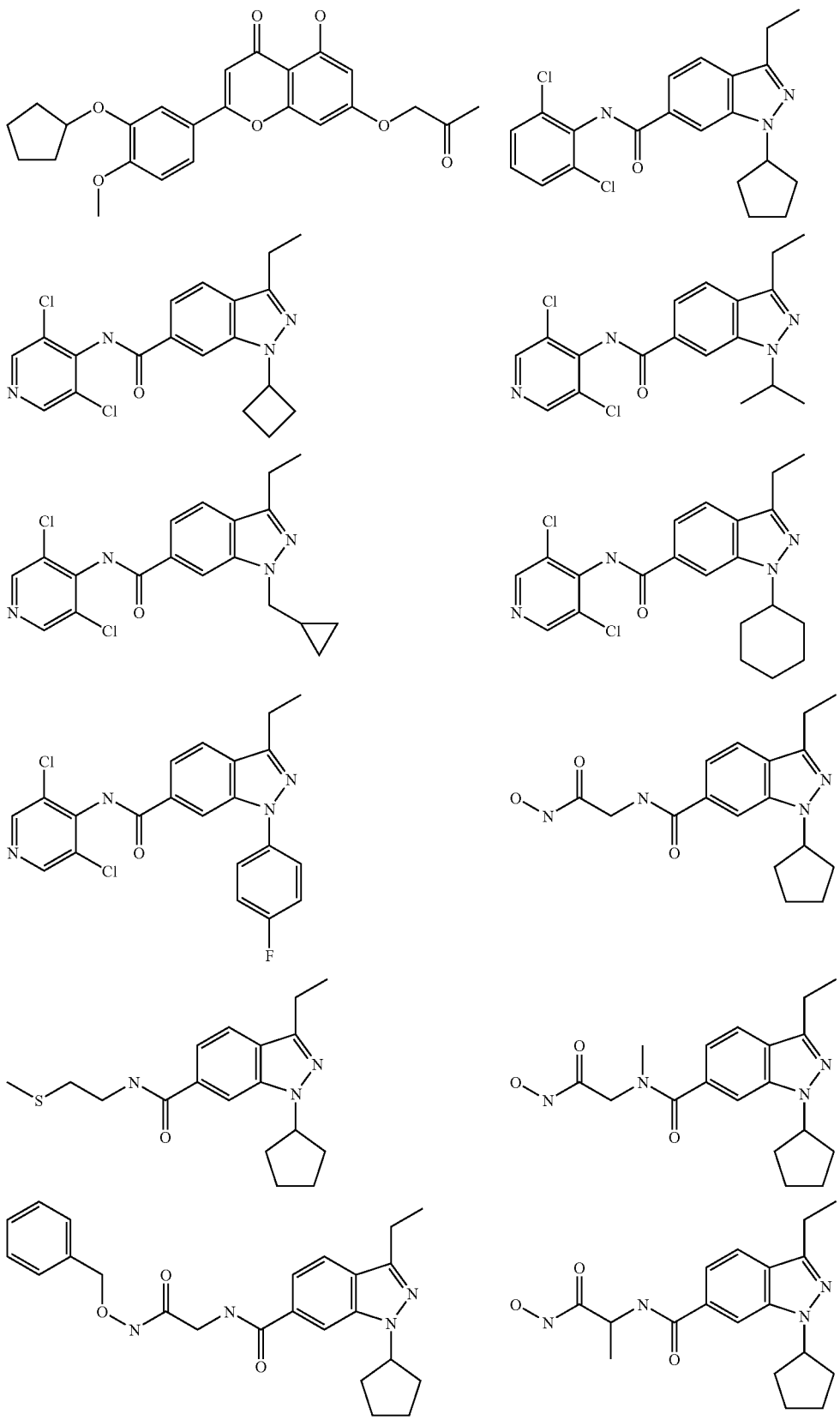

-continued
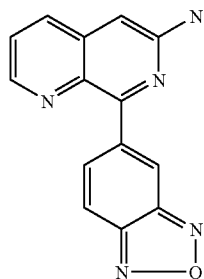
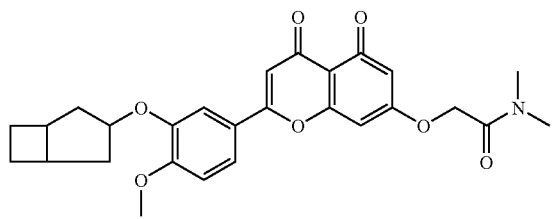
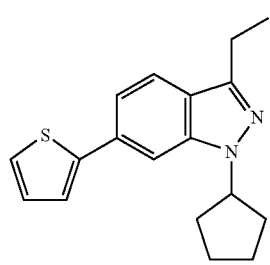
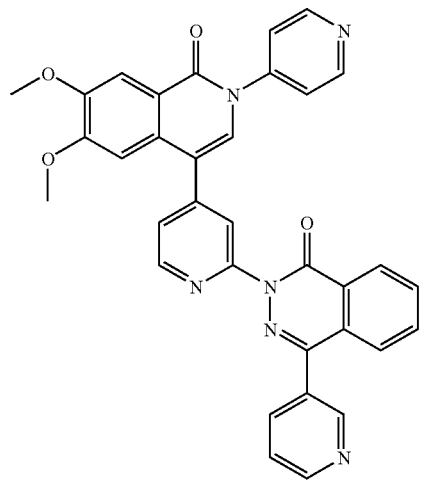
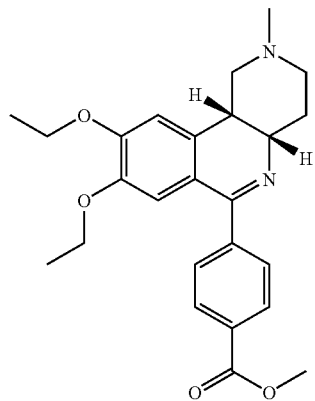
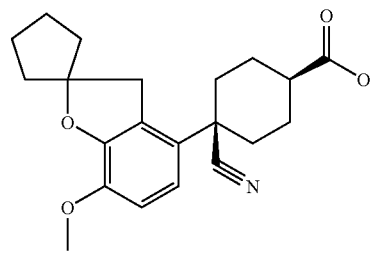
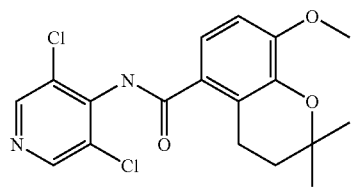
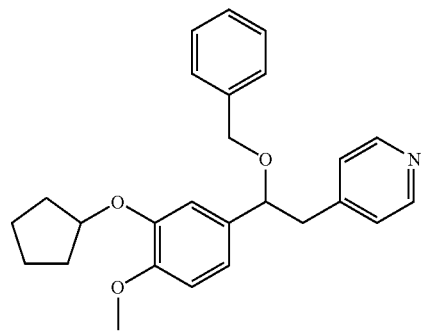

-continued
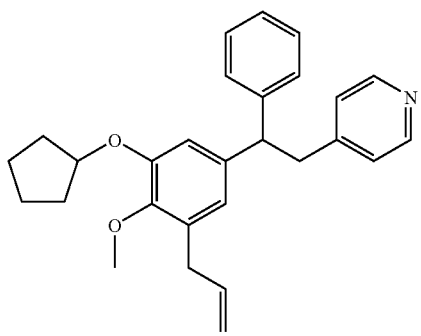
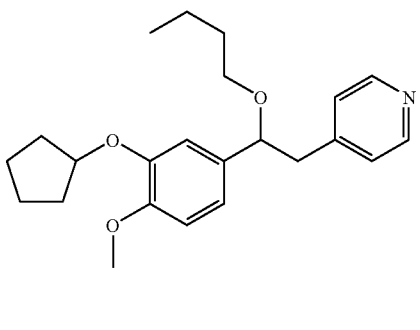
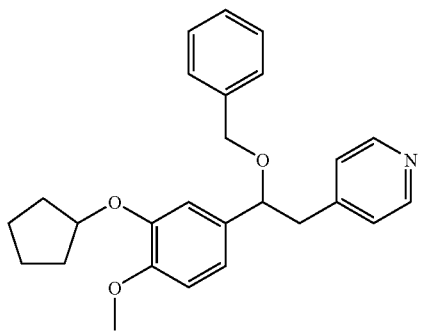
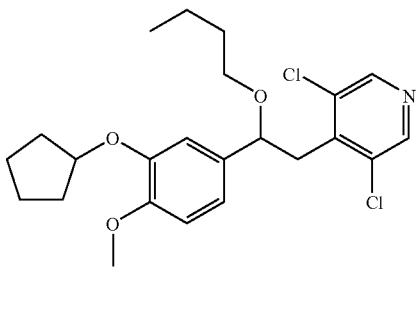
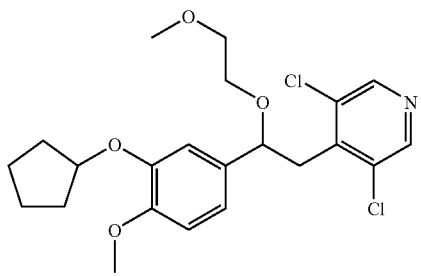
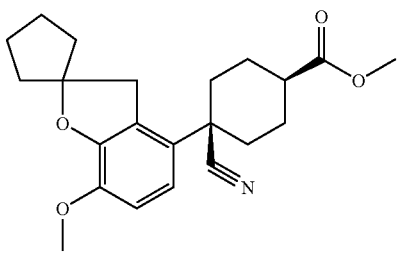
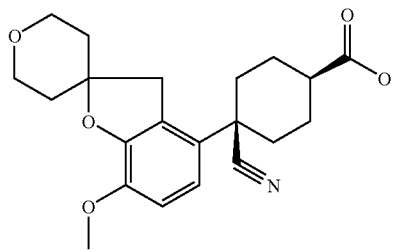
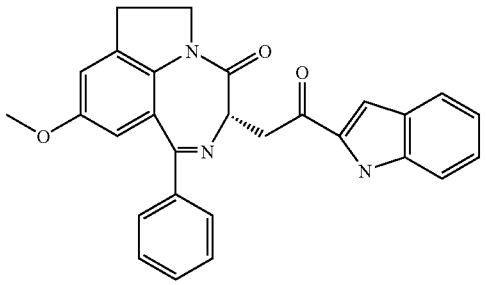
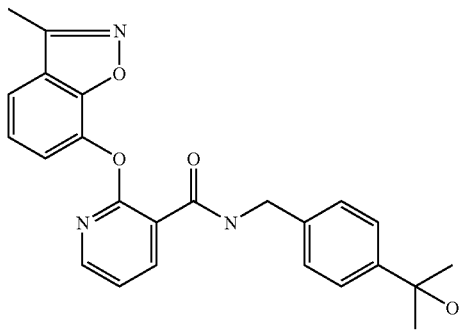
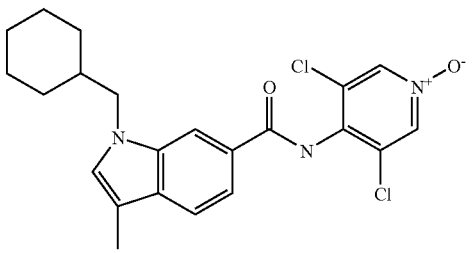

-continued
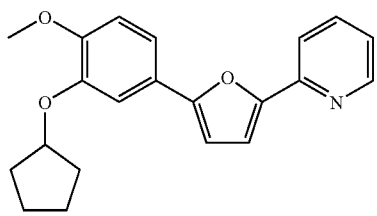
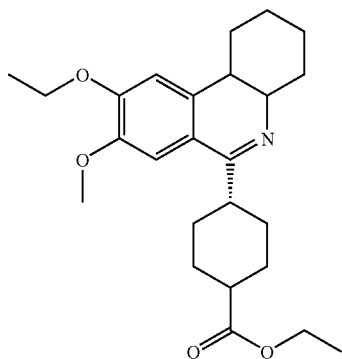
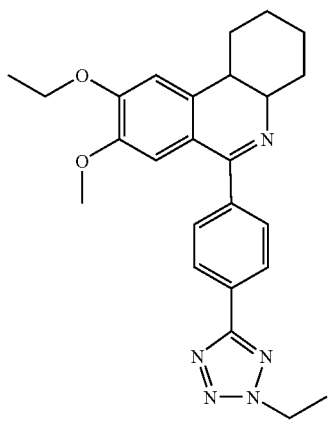
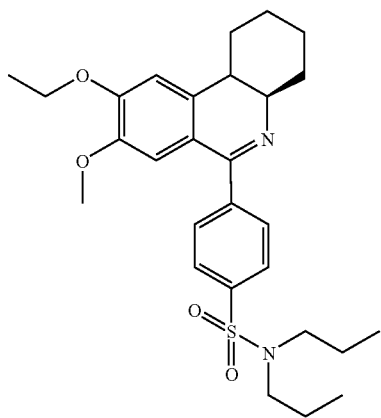
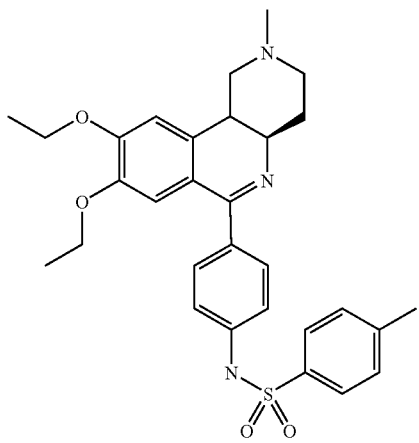
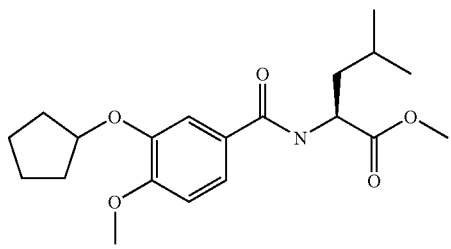
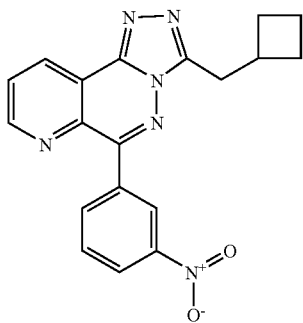
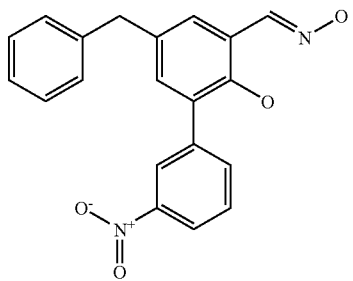

-continued
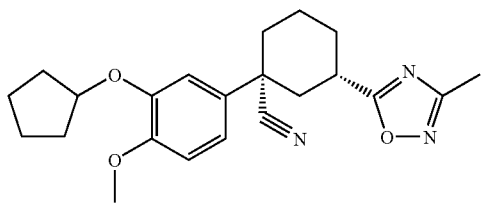
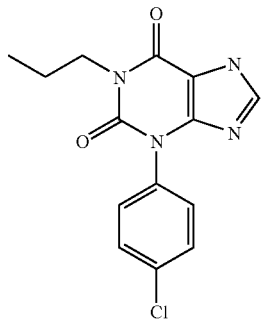
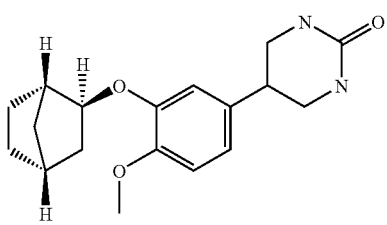
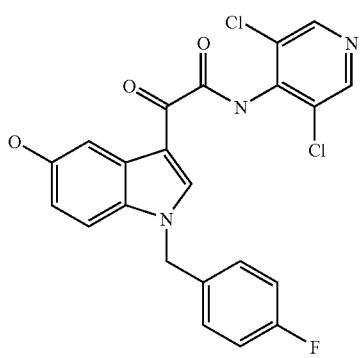
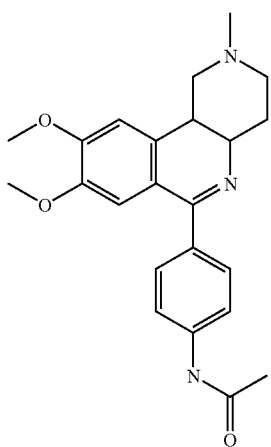
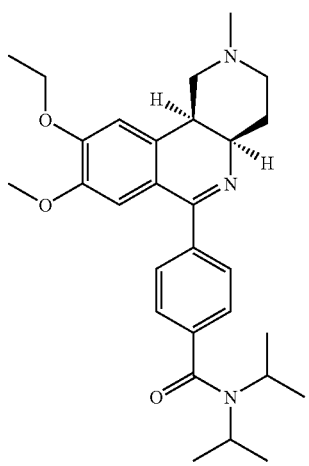
BYK-33043
(Pumafentrin)
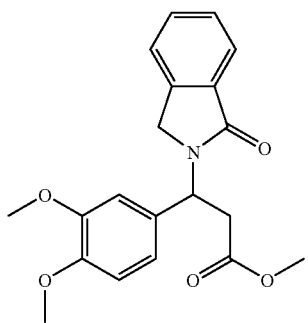
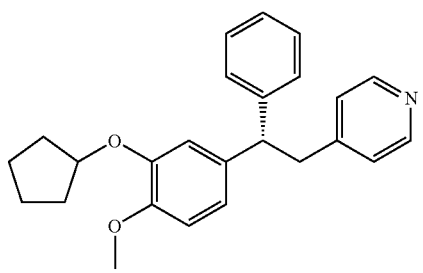

-continued
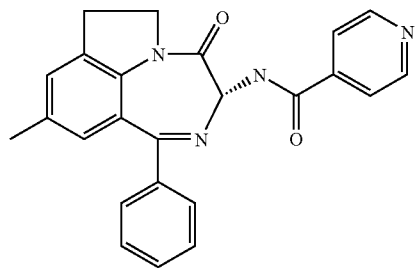
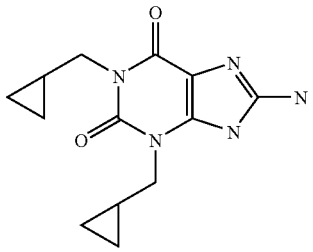
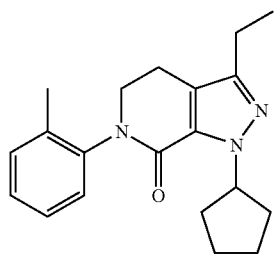
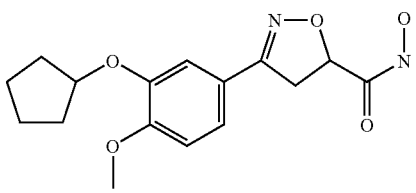
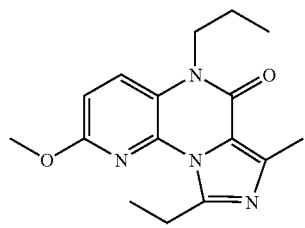
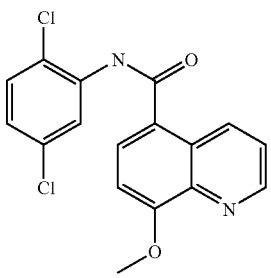
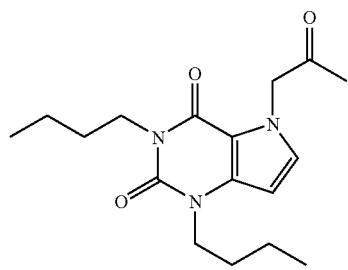
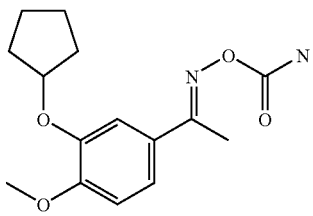
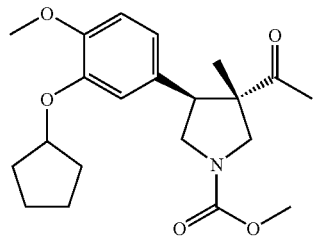
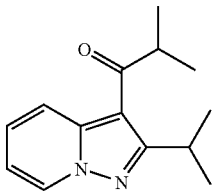
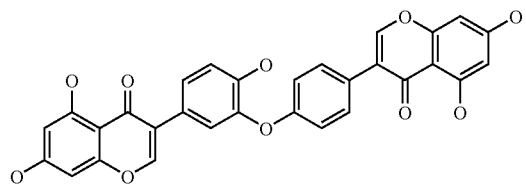
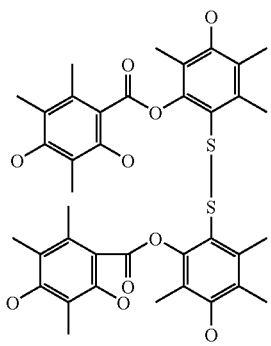

-continued
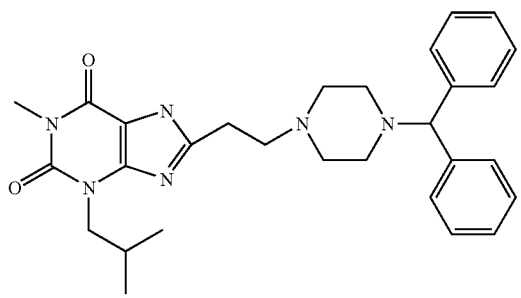
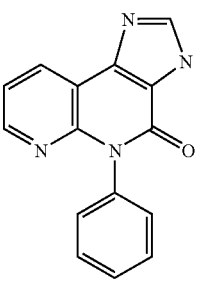
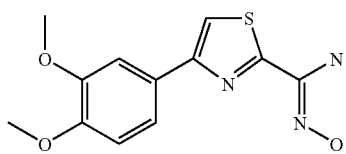
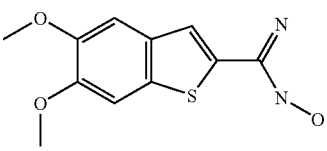
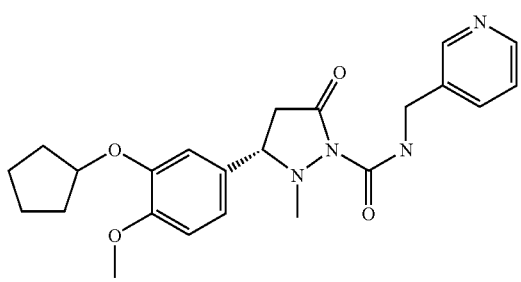
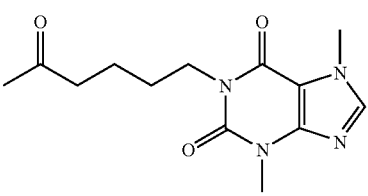
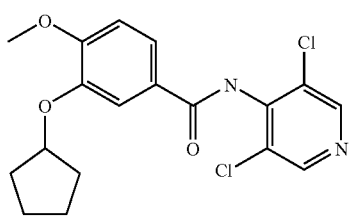
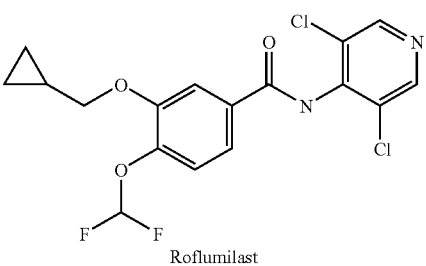
Roflumilast
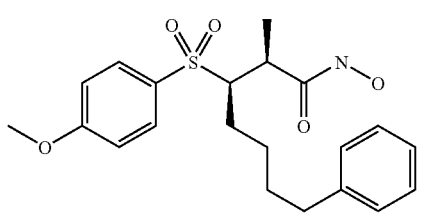
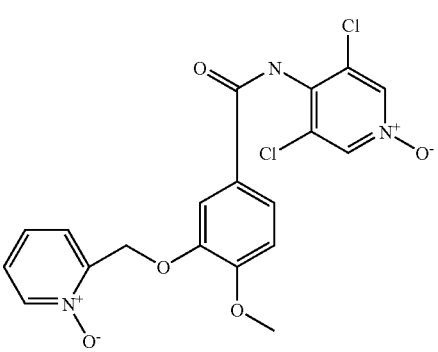
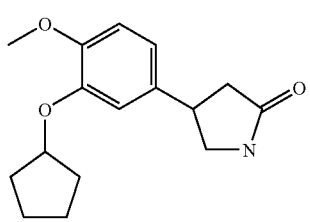
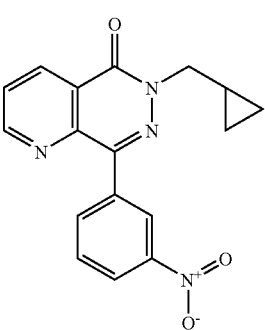

-continued
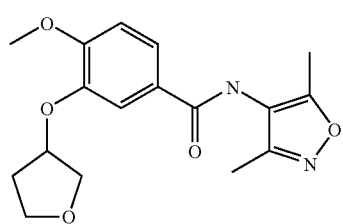
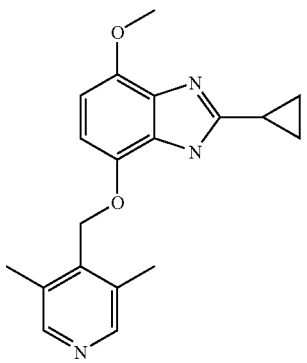
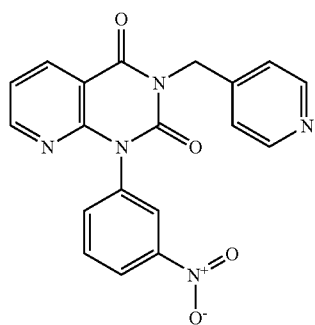
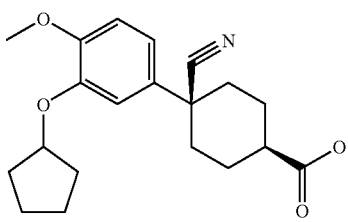
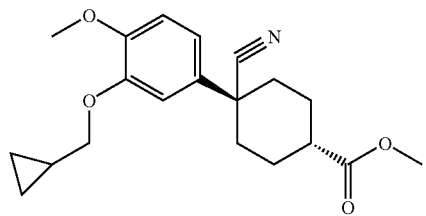
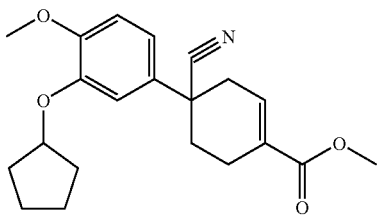
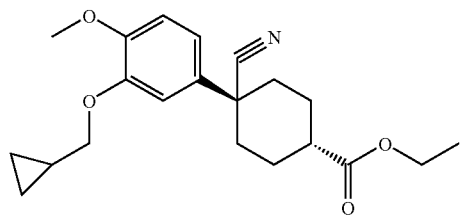
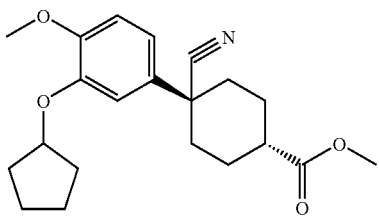
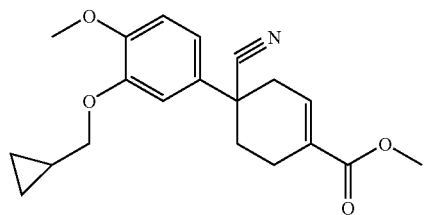
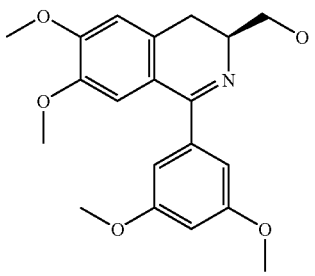
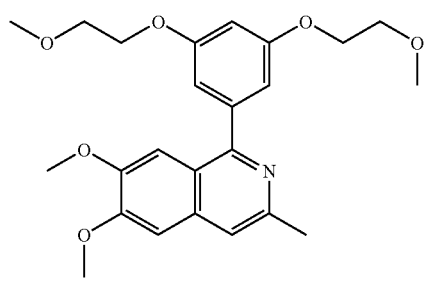
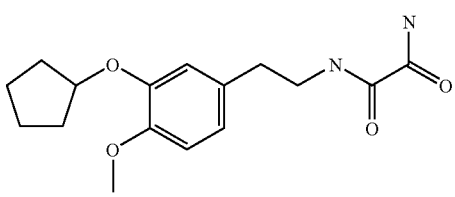

47
48
-continued
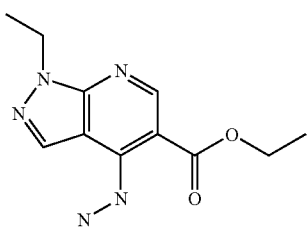
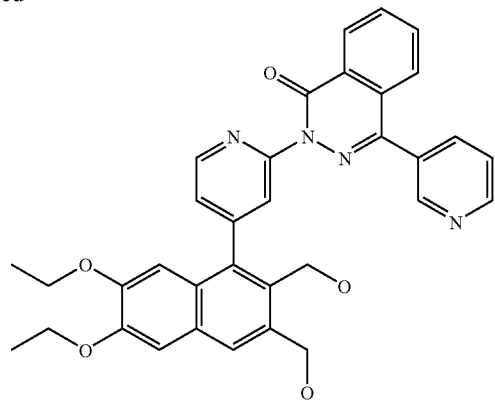
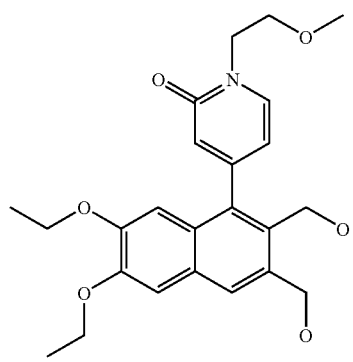
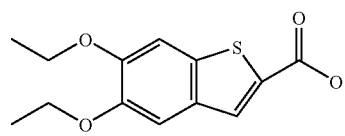
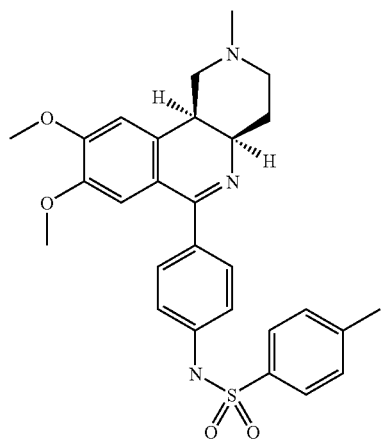
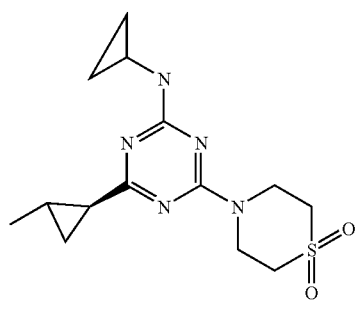
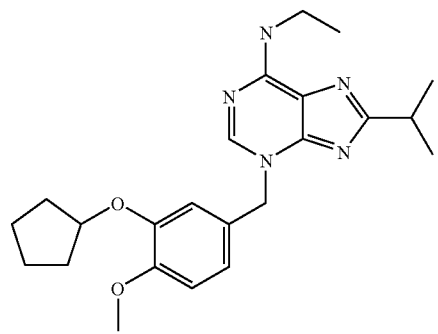

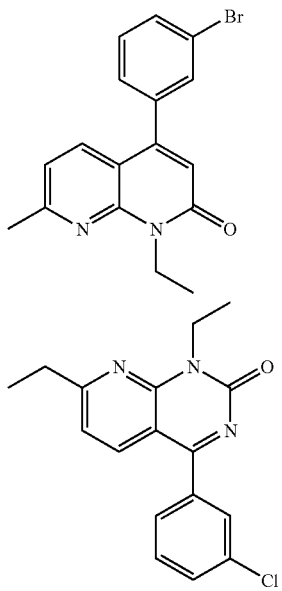

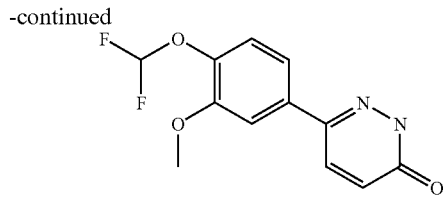

No hydrogen atoms are indicated in the above formulae. —O is accordingly —OH, —N is NH$_2$. Methyl groups, e.g. on the oxygen atoms, are indicated by lines.

PDE inhibitors to be emphasized which are selected from the abovementioned compounds and which may be mentioned are the active compounds arofylline, atizoram, AWD-12-281, BAY-19-8004, benafentrine, BYK-33043, CC-3052, CDP-840, CI-1018, cipamfylline, CP-220629, CP-293121, D-22888, D-4396, D-4418, denbufylline, filaminast, GW-3600, ibudilast, KF-17625, KS-506-G, laprafylline, NA-0226A, NA-23063A, ORG-20241, ORG-30029, PDB-093, pentoxifylline, piclamilast, roflumilast, rolipram, RPR-117658, RPR-122818, RPR-132294, RPR-132703, RS-17597, RS-25344-000, SB-207499, SB-210667, SB-211572, SB-211600, SB-212066, SB-212179, SDZ-ISQ-844, SDZ-MNS-949, SKF-107806, SQ-20006, T-2585, T-440, tibenelast, tolafentrine, UCB-29646, V-11294A, YM-58997, YM-976 and zardaverine.

The compounds preferred from the group of the abovementioned PDE inhibitors are arofylline, cipamfylline, D-4418, filaminast, ibudilast, laprafylline, ORG-20241, piclamilast, rolipram, SB-207499, tibenelast and V-11294A. The compounds particularly preferred are BYK-33043 and in particular roflumilast.

β$_2$ adrenoceptor agonists which may particularly be mentioned are those selectively acting substances which only have a slight cardiac action and therefore are also employed in therapy, in particular in the oral therapy of respiratory tract disorders. β$_2$ adrenoceptor agonists which may be mentions are, for example: 4-hydroxy-7-[2-[2-[3-phenylethoxypropane-1sulfonyl]ethylamino]ethyl]-3H-benzothiazol-2-one, hydrochloride (AR-C68397AA), 1-(3-bromo-5-isoxazolyl)-2-tert-butyl aminoethanol (broxaterol), rac-5,6-diisobutyryloxy-2-methylamino-1,2,3,4-tetrahydronaphthalene hydrochloride (CHF-1035), 1-(2-chloro-4-hydroxyphenyl)-2-tert-butylaminoethanol (HOKU-81), 1-(3,5-dihydroxyphenyl)-2-(tert-butylamino)ethanol diisobutyrate ester (ibuterol), KUL-1248, N-[2-hydroxy-5-[1-hydroxy-2-[(1-methylethyl) amino]ethyl]phenyl]methanesulfonamide (soterenol), 4-(2-tert-butylamino-1-hydroxyethyl)-3-chlorophenol (meluadrine), 8-hydroxy-5-[(1R)-1-hydroxy-2-[N-[(1R)-2-(p-methoxyphenyl)-1-methylethyl]aminol]ethyl]carbostyril hydrochloride (TA-2005), 5-chloro-3-[4-(2- hydroxyethyl)-1-piperazinyl]carbonylmethyl-2-benzothiazolinone (tiaramide), 4-hydroxy-3-hydroxymethyl-α-[(tert-butylamino)methyl] benzyl alcohol (salbutamol), (R)-4-hydroxy-3-hydroxymethyl-α-[(tert-butylamino)methyl]benzyl alcohol (levosalbutamol),(2-chiorophenyl)-1-tert-butylamino-2-ethanol (tulobuterol),1-(3,5-dihydroxyphenyl)-2-(tert-butylamino) ethanol (terbutaline), [5-[2-[(1,1-dimethylethyl)amino]-1-hydroxyethyl]-2-hydroxyphenyl]urea (carbuterol), 2-hydroxymethyl-3-hydroxy-6-(1-hydroxy-2-tert-butylaminoethyl) pyridine (pirbuterol), 7-[3-[[2-(3,5-dihydroxyphenyl)-2-hydroxyethyl]amino]propyl]-3,7-dihydro-1,3-dimethyl-1H-purine-2,6-dione (reproterol), 4-amino-3,5-dichloro-α-[[(1,1- dimethylethyl)amino]methyl]benzenemethanol (clenbuterol), 1-(3,5-dihydroxyphenyl)-1-hydroxy-2-[(4-hydroxyphenyl) isopropylamino]ethane (fenoterol), N,N'-bis[2-(3,4-dihydroxyphenyl)-2-hydroxyethyl]hexamethylenediamine (hexoprenaline), 1-(3,5-dihydroxyphenyl)-2-isopropylaminoethanol hemisulfate (orciprenaline), 4-[1-hydroxy-2-[(1-methylethyl)amino]ethyl]-1,2-benzenediol (isoprenaline), (R*,R*)-(+)-N-[2-hdroxy-5-[1-hydroxy-2-[[2-(4-methoxyphenyl)-1-methylethyl]amino]ethyl]phenyl] formamide (formoterol), (+)-4-hydroxy-α$^1$-[[[6-(4-phenylbutoxy) hexyl]amino]methyl]-1,3-benzenedimethanol (saimeterol), 4-(hydroxy-2-piperidinylmethyl)-1,2-benzenediol (rimiterol), (R*,S*)–(+)-8-hydroxy-5-[1-hydroxy-2-[(1-methylethyl)amino]butyl](1H)-quinolinone (procaterol), dimethylcarbamic acid 5-[2-[(1,1-dimethyiethyl)aminol]-1-hydroxyethyl]-1,3-phenylene ester (bambuterol), 4-methylbenzoic acid 4-[2-[(1,1-dimethylethyl)amino]-1-hydroxyethyl]-1,2- phenylene ester (bitolterol) and 4-amino-3-chloro-α-[[(1,1-dimethylethyl)amino]methyl]-5-(trifluoromethyl)bezenemethanol (mabuterol). The orally ready available β$_2$ adrenoceptor agonists such as clenbuterol, orciprenalifle, salbutamol, terbutaline, tulobuterol, bambuterol and reproterol are preferred. Particularly preferred are the so called long acting β$_2$ adrenoceptor agonists, such as salmeterol.

The PDE inhibitors and the β$_2$ adrenoceptor agonists can be present as such or in chemically bonded form. It is understood hereby that the active compounds mentioned can also be present, for example, in the form of their pharmacologically tolerable salts and/or as solvates (e.g. hydrates), and/or in the form of their N-oxides etc. Suitable pharmacologically tolerable salts here are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid, the acids being employed in salt preparation—depending on whether it is a mono- or polybasic acid and depending on which salt is desired—in an equimolar quantitative ratio or one differing therefrom. Furthermore, the active compounds mentioned can also be present as pure enantiomers or as enantiomer mixtures in any mixing ratio.

Respiratory tract disorders which may be mentioned are in particular allergen- and inflammation-induced bronchial disorders (bronchitis, obstructive bronchitis, spastic bronchitis, allergic bronchitis, allergic asthma, bronchial asthma, COPD), which can be treated by the combination according to the invention also in the sense of a long-term therapy (if desired with appropriate adjustment of the dose of the individual components to the needs at the time, for example needs subject to seasonally related variations).

"Combined use" or "combination" within the meaning of the present invention is to be understood as meaning that the individual components can be administered simultaneously (in the form of a combination medicament), more or less simultaneously (from separate pack units) or in succession (directly in succession or else alternatively at a relatively large time interval) in a manner which is known per se and customary.

Within the meaning of the present invention, "use" is preferably understood as meaning the oral administration of both active compounds. If only the PDE inhibitor is administered orally, "use" with respect to the $\beta_2$ adrenoceptor agonist is understood in particular as meaning topical application in inhalatory form. For this, the $\beta_2$ adrenoceptor agonist is preferably administered by inhalation in the form of an aerosol, the aerosol particles of solid, liquid or mixed composition having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

The active compounds are dosed in an order of magnitude customary for the individual dose, it more likely being possible, on account of the individual actions, which are mutually positively influencing and reinforcing, to reduce the respective doses on the combined administration of the active compounds compared with the norm. Customarily, the $\beta_2$ adrenoceptor agonist (depending on potency) is administered in a dose of, for example, 0.002 to 2.0 mg per day on administration by inhalation.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

In the case of the oral administration of the $\beta_2$ adrenoceptor agonists together with the PDE inhibitor, which is the preferred administration form, the $\beta_2$ adrenoceptor agonist is administered in a daily dose of, for example, 0.05 to 60 mg. For the PDE inhibitors, it is possible in the case of oral administration to vary the doses—depending on the active compound—within a wide range, it being possible, as bounds, to start from a dose of 1-2000 µg/kg of body weight. In the case of the administration of the preferred PDE inhibitor roflumilast, the dose is in the range from 2–20 µg/kg of body weight.

The PDE inhibitors to be administered orally are formulated—if appropriate together with the $\beta_2$ adrenoceptor agonists—to give medicaments according to processes known per se and familiar to the person skilled in the art. The pharmacologically active compounds are employed as medicaments, preferably in combination with suitable pharmaceutical excipients or vehicles, in the form of tablets, coated tablets, capsules, emulsions, suspensions or solutions, the active compound content advantageously being between 0.1 and 95% and, by the appropriate choice of the excipients and vehicles, it being possible to achieve a pharmaceutical administration form precisely tailored to the active compound(s) and/or to the desired onset of action (e.g. a sustained-release form or an enteric form). Particularly worthy of mention within the meaning of the combined, oral administration of both active compounds according to the invention are oral administration forms, e.g. tablets or capsules, in which one part of the $\beta_2$ adrenoceptor agonist and the PDE inhibitor is present in non sustained-release form and a further, preferably larger part, of the $\beta_2$ adrenoceptor agonist is present in sustained-release form.

The person skilled in the art is familiar on the basis of his/her expert knowledge with which excipients or vehicles are suitable for the desired pharmaceutical formulations. In addition to solvents, gel-forming agents, tablet excipients and other active compound carriers, it is possible to use, for example, antioxidants, dispersants, emulsifiers, antifoams, flavor corrigents, preservatives, solubilizers, colorants or permeation promoters and complexing agents (e.g. cyclodextrins).

Pharmacology

Model

Late Inflammatory Airway Reaction in the Ovalbumin-sensitized/-challenged Brown-Norway Rat Anti-inflammatory activity of Roflumilast, Pumafentrine (BYK-33043), and Salmeterol was determined in ovalbumin (OVA)-sensitized and OVA-challenged Brown Norway rats. Sensitization was done by simultaneous injection of Bordetella pertussis suspension i.p. and OVA/AHG suspension s.c. on day 1, 14 and 21. 28 days after start of sensitization, conscious Brown-Norway rats were challenged by inhalation of the aerosolized OVA solution for 1 h (~20 ml/h). Non-challenged, only sensitized animals were used as baseline control. The drugs (thoroughly mixed with lactose) or the placebo control (lactose) were administered intratracheally (i.t.) as dry powders 1 h before OVA-challenge. 48 h later, OVA-challenged or non-challenged animals were anaesthetized and bronchoalveolar lavage (BAL) was performed using 3×4 ml BAL buffer per animal. The number of total cells and eosinophils in the BAL fluid, and the concentration of protein in the cell-free BAL fluid were determined. Drug-induced relative changes were calculated and statistically analyzed by the Jonckheere Terpstra test.

| | | | | | Results | | |
|---|---|---|---|---|---|---|---|
| | | | | | | % Inhibition of Infiltration/Accumulation [Median/ Mean ± SEM] | |
| Compound | PDE3/4 IC50[μmol] | Dose [μmol/kg] | Appl. Route | N | Total cells | EOS | Protein |
| Roflumilast | >10/0.0007 | 0.3 | it | 8 | −25 | −15 | −8 |
| | | | | | −37.6 ± 26.7 | −22 ± 25.7 | −22.3 ± 25.5 |
| Pumafentrine | 0.028/0.007 | 3 | it | 8 | −19 | −26 | 17 |
| | | | | | −39.1 ± 30.5 | −28.5 ± 30.1 | 23.5 ± 10.6 |
| Salmeterol | | 3 | it | 8 | 19 | 39 | 44 |
| | | | | | 6.3 ± 17.9 | 31 ± 14.8 | 37.5 ± 16.2 |
| Salmeterol/ Roflumilast | | 3/0.3 | it | 8 | 50 | 67 ** | 59 ** |
| | | | | | 34.5 ± 21.1 | 61.1 ± 7.9 ** | 50.8 ± 13.6 ** |
| Salmeterol/ Pumafentrine | | 3/3 | it | 8 | 56 * | 85 ** | 75 ** |
| | | | | | 58.1 ± 12.3 * | 83 ± 3.7 ** | 67.1 ± 11.1 ** |

* $p < 0.05$
** $p < 0.01$ v.s. untreated, OVA—challenged control groups

SUMMARY

The PDE inhibitors Roflumilast (PDE4 inhibitor) and Pumafentrine (PDE3>4 inhibitor) administered at doses of 0.3 μmol/kg and 3 μmol/kg i.t., respectively, did not show any significant effects on cell infiltration and protein accumulation. The negative values obtained (trend: amplification of inflammation) fall into the range of biological variability of the model and therefore, no significance must be attached to these data.

In contrast, the long-acting β2-adrenergic receptor agonist Salmeterol given at a dose of 3 pmol/kg i.t exhibited inhibitory effects on total cell and eosinophil influx into alveolar space and protein levels in BAL fluid. However, the data failed to reach significance.

Co-administration of the PDE inhibitor Roflumilast or Pumafentrine with Salmeterol resulted in synergistic effects compared to administration of every compound alone, i.e. both PDE inhibitors combined with the β2 agonist displayed a significant inhibition of eosinophilia and reduction of protein concentration in the BAL fluid. The combination of the PDE3/4 inhibitor Pumafentrine and Salmeterol was more efficacious on all parameters measured (difference was not significant), and additionally, showed a significant effect on inhibition of total cell influx into the alveolar space.

The invention claimed is:

1. A pharmaceutical composition comprising a PDE inhibitor, which is to be administered orally, from the PDE4 or PDE3/4 inhibitors group combined with a $β_2$ adrenoceptor agonist in fixed or free combination, wherein said PDE inhibitor is roflumilast or a pharmacologically tolerable salt thereof and wherein said $β_2$ adrenoceptor agonist is (±)-4-hydroxy-$α^1$-[[[6-(4-phenylbutoxy)hexyl]amino]methyl]-1,3-benzenedimethanol or a pharmacologically tolerable salt thereof.

2. The pharmaceutical composition as claimed in claim 1, which is a fixed oral combination.

3. The pharmaceutical composition as claimed in claim 1, which additionally contains an excipient selected from the group consisting of propellants, surface-active substances, emulsifiers, stabilizers, preservatives, flavorings, fillers, solvents, gel-forming agents, tablet excipients, antioxidants, dispersants, antifoams, flavor corrigents, solubilizers, colorants or permeation promoters, and complexing agents.

4. A method of treating a respiratory tract disorder in a patient, comprising administering a therapeutically effective amount of a PDE inhibitor from the PDE4-or PDE3/4 inhibitors group in combination with a $β_2$ adrenoceptor agonist to said patient, wherein said PDE inhibitor is administered orally, wherein said PDE inhibitor is roflumilast or a pharmacologically tolerable salt thereof and wherein said $β_2$ adrenoceptor agonist is (±)-4-hydroxy-$α^1$-[[[6-(4-phenylbutoxy)hexyl]amino]methyl]-1,3-benzenedimethanol or a pharmacologically tolerable salt thereof.

5. The method of claim 4, wherein the respiratory tract disorder is an allergen-induced or inflammation-induced bronchial disorder.

6. The method of claim 5, wherein the allergen-induced or inflammation-induced bronchial disorder is selected from the group consisting of bronchitis, obstructive bronchitis, spastic bronchitis, allergic bronchitis, allergic asthma, bronchial asthma, and COPD.

7. The method of claim 4, wherein the PDE inhibitor and the $β_2$ adrenoceptor agonist are administered simultaneously.

8. The method of claim 4, wherein the PDE inhibitor and the $β_2$ adrenoceptor agonist are administered more or less simultaneously.

9. The method of claim 4, wherein the PDE inhibitor and the $β_2$ adrenoceptor agonist are administered in succession.

* * * * *